US011118226B2

(12) United States Patent
Matthiesen

(10) Patent No.: US 11,118,226 B2
(45) Date of Patent: Sep. 14, 2021

(54) HYBRIDIZATION COMPOSITIONS AND METHODS

(71) Applicant: Agilent Technologies, Inc., Santa Clara, CA (US)

(72) Inventor: Steen Hauge Matthiesen, Hilleroed (DK)

(73) Assignee: AGILENT TECHNOLOGIES, INC., Santa Clara, CA (US)

( * ) Notice: Subject to any disclaimer, the term of this patent is extended or adjusted under 35 U.S.C. 154(b) by 155 days.

(21) Appl. No.: 14/352,815

(22) PCT Filed: Oct. 22, 2012

(86) PCT No.: PCT/EP2012/070877
§ 371 (c)(1),
(2) Date: Apr. 18, 2014

(87) PCT Pub. No.: WO2013/057310
PCT Pub. Date: Apr. 25, 2013

(65) Prior Publication Data
US 2014/0242589 A1 Aug. 28, 2014

Related U.S. Application Data

(60) Provisional application No. 61/550,016, filed on Oct. 21, 2011.

(51) Int. Cl.
*C12Q 1/6841* (2018.01)
*C12Q 1/6881* (2018.01)
*C12Q 1/6832* (2018.01)

(52) U.S. Cl.
CPC ......... *C12Q 1/6881* (2013.01); *C12Q 1/6832* (2013.01); *C12Q 1/6841* (2013.01)

(58) Field of Classification Search
None
See application file for complete search history.

(56) References Cited

U.S. PATENT DOCUMENTS

| | | |
|---|---|---|
| 4,652,517 A | 3/1987 | Scholl et al. |
| 4,886,741 A | 12/1989 | Schwartz |
| 4,888,278 A | 12/1989 | Singer et al. |
| 4,996,359 A | 2/1991 | Kesling, Jr. et al. |
| 5,106,730 A | 4/1992 | Van Ness et al. |
| 5,132,207 A | 7/1992 | Kohne et al. |
| 5,382,285 A | 1/1995 | Morrison |
| 5,432,065 A | 7/1995 | Fuller |
| 5,521,061 A | 5/1996 | Bresser et al. |
| 5,525,492 A | 6/1996 | Hill |
| 5,527,675 A | 6/1996 | Coull et al. |
| 5,539,082 A | 7/1996 | Nielsen et al. |
| 5,582,985 A | 12/1996 | Thompson |
| 5,623,049 A | 4/1997 | Obberding et al. |
| 5,633,129 A | 5/1997 | Karger et al. |
| 5,650,148 A | 7/1997 | Gage et al. |
| 5,705,333 A | 1/1998 | Shah et al. |
| 5,714,331 A | 2/1998 | Buchardt et al. |
| 5,718,915 A | 2/1998 | Virtanen et al. |
| 5,736,336 A | 4/1998 | Buchardt et al. |
| 5,750,340 A | 5/1998 | Kim et al. |
| 5,766,855 A | 6/1998 | Buchardt et al. |
| 5,773,571 A | 6/1998 | Nielsen et al. |
| 5,786,461 A | 7/1998 | Buchardt et al. |
| 5,837,459 A | 11/1998 | Berg et al. |
| 5,856,089 A | 1/1999 | Wang et al. |
| 5,858,671 A | 1/1999 | Jones |
| 5,869,237 A | 2/1999 | Ward et al. |
| 5,891,625 A | 4/1999 | Buchardt et al. |
| 5,919,894 A | 7/1999 | Schubart |
| 5,925,744 A | 7/1999 | Haner et al. |
| 5,962,227 A | 10/1999 | Hedrick et al. |
| 5,972,610 A | 10/1999 | Buchardt et al. |
| 5,986,053 A | 11/1999 | Ecker et al. |
| 6,107,470 A | 8/2000 | Nielsen et al. |
| 6,201,103 B1 | 3/2001 | Nielsen et al. |
| 6,203,977 B1 | 3/2001 | Ward et al. |
| 6,228,982 B1 | 5/2001 | Norden et al. |
| 6,331,618 B1 | 12/2001 | Bloch et al. |
| 6,344,315 B1 | 2/2002 | Gray et al. |
| 6,357,163 B1 | 3/2002 | Buchardt et al. |
| 6,361,940 B1 | 3/2002 | Van Ness et al. |
| 6,475,720 B1 | 11/2002 | Gray et al. |
| 6,555,670 B1 | 4/2003 | Aizawa et al. |
| 6,586,176 B1 | 7/2003 | Trnovsky et al. |
| 6,656,685 B2 | 12/2003 | Utermohlen et al. |
| 6,656,734 B1 | 12/2003 | Bischoff et al. |

(Continued)

FOREIGN PATENT DOCUMENTS

| | | |
|---|---|---|
| EA | 005581 B1 | 4/2005 |
| EP | 0261955 A2 | 3/1988 |

(Continued)

OTHER PUBLICATIONS

International Search Report for International Application No. PCT/EP2012/070877, dated Jun. 4, 2013 (5 pages).
Office Communication from the European Patent Office dated Jun. 12, 2015.
Acloque, et al., "In Situ Hybridization Analysis of Chick Embryos in Whole-Mount and Tissue Sections", Methods in Cell Biology, vol. 82, No. 169, 2008, 17 pages.
Ahern, "Biochemical, Reagents Kits Offer Scientists Good Return on Investment", The Scientist vol. 9, No. 15, Jul. 24, 1995, 20 pages.
Ahern, "DNA, RNA Probes Help Investigators Narrow the Search for Genes", The Scientist Magazine®, Nov. 27, 1995, 7 pages.

(Continued)

*Primary Examiner* — Robert T. Crow

(57) ABSTRACT

The invention provides methods and compositions for hybridizing at least one molecule to a target. The invention may, for example, utilize a of cyclic and/or non-cyclic solvent that is non-toxic and may eliminate or reduce the amount of formamide in the hybridization composition.

20 Claims, 1 Drawing Sheet

(56) References Cited

U.S. PATENT DOCUMENTS

| | | |
|---|---|---|
| 6,670,461 B1 | 12/2003 | Wengel et al. |
| 6,794,499 B2 | 9/2004 | Wengel et al. |
| 6,949,368 B2 | 9/2005 | Chakrabarti et al. |
| 7,034,133 B2 | 4/2006 | Wengel et al. |
| 7,105,294 B2 | 9/2006 | Van Dongen et al. |
| 7,329,491 B2 | 2/2008 | Kirchgesser et al. |
| 7,374,945 B2 | 5/2008 | Becker |
| 7,572,582 B2 | 8/2009 | Wengel et al. |
| 7,655,422 B2 | 2/2010 | Adler et al. |
| 7,750,208 B2 | 7/2010 | Huang et al. |
| 7,867,443 B2 | 1/2011 | Key et al. |
| 7,901,634 B2 | 3/2011 | Testa et al. |
| 8,034,909 B2 | 10/2011 | Wengel et al. |
| 8,080,644 B2 | 12/2011 | Wengel et al. |
| 8,153,365 B2 | 4/2012 | Wengel et al. |
| 8,211,385 B2 | 7/2012 | Testa et al. |
| 8,632,739 B2 | 1/2014 | Winther et al. |
| 8,877,144 B2 | 11/2014 | Poulsen et al. |
| 9,133,507 B2 | 9/2015 | Testa et al. |
| 9,182,323 B2 | 11/2015 | Poulsen et al. |
| 9,297,035 B2 | 3/2016 | Matthiesen et al. |
| 9,303,287 B2* | 4/2016 | Matthiesen .......... C12Q 1/6832 |
| 9,309,562 B2* | 4/2016 | Matthiesen .......... C12Q 1/6832 |
| 9,388,456 B2 | 7/2016 | Matthiesen |
| 9,388,466 B2 | 7/2016 | Chen et al. |
| 10,202,638 B2 | 2/2019 | Matthiesen |
| 10,662,465 B2 | 5/2020 | Matthiesen |
| 2001/0000487 A1 | 4/2001 | Essenfeld et al. |
| 2001/0007748 A1 | 7/2001 | An et al. |
| 2001/0009766 A1 | 7/2001 | Bard et al. |
| 2001/0010936 A1 | 8/2001 | Richards et al. |
| 2001/0011131 A1 | 8/2001 | Luyten et al. |
| 2001/0018512 A1 | 8/2001 | Blanchard |
| 2001/0026919 A1 | 10/2001 | Chenchik et al. |
| 2001/0027567 A1 | 10/2001 | Federoff |
| 2001/0056203 A1 | 12/2001 | Sezi et al. |
| 2002/0006652 A1 | 1/2002 | Danielsen et al. |
| 2002/0019001 A1 | 2/2002 | Light |
| 2002/0058278 A1 | 5/2002 | Stefano et al. |
| 2002/0065224 A1 | 5/2002 | Bender et al. |
| 2002/0076809 A1 | 6/2002 | Steinmeyer et al. |
| 2002/0119465 A1 | 8/2002 | Zhao et al. |
| 2002/0127569 A1 | 9/2002 | Weisburg et al. |
| 2002/0150904 A1 | 10/2002 | Bi et al. |
| 2002/0164589 A1* | 11/2002 | Taylor ............................... 435/6 |
| 2002/0164614 A1 | 11/2002 | Becker |
| 2002/0182613 A1 | 12/2002 | Mirkin et al. |
| 2002/0197629 A1 | 12/2002 | Gjerde et al. |
| 2002/0198366 A1 | 12/2002 | Ashkenazi et al. |
| 2003/0108903 A1 | 6/2003 | Wang et al. |
| 2003/0125312 A1 | 7/2003 | Rocha et al. |
| 2003/0134279 A1 | 7/2003 | Isola et al. |
| 2003/0175852 A1 | 9/2003 | Kalra et al. |
| 2003/0203391 A1* | 10/2003 | Sana .................... C12Q 1/6832 435/6.16 |
| 2004/0029184 A1 | 2/2004 | Gourevitch |
| 2004/0030093 A1 | 2/2004 | Sakurai et al. |
| 2004/0048376 A1 | 3/2004 | Chabot et al. |
| 2004/0053222 A1 | 3/2004 | Storhoff et al. |
| 2004/0096856 A1 | 5/2004 | Garimella et al. |
| 2004/0096967 A1 | 5/2004 | Gryseels et al. |
| 2004/0101946 A1 | 5/2004 | Hovanec |
| 2004/0106109 A1 | 6/2004 | Belly et al. |
| 2004/0122101 A1 | 6/2004 | Miller et al. |
| 2004/0210967 A1 | 10/2004 | Chen et al. |
| 2004/0219546 A1 | 11/2004 | Sakaki et al. |
| 2004/0224343 A1 | 11/2004 | Han et al. |
| 2004/0241666 A1 | 12/2004 | Amorese et al. |
| 2004/0248790 A1 | 12/2004 | Hinuma et al. |
| 2004/0268439 A1 | 12/2004 | Cheng et al. |
| 2005/0014154 A1 | 1/2005 | Weizenegger |
| 2005/0064472 A1 | 3/2005 | Shekar et al. |
| 2005/0079535 A1 | 4/2005 | Kirchgesser et al. |
| 2005/0191657 A1 | 9/2005 | Demorest |
| 2005/0234236 A1 | 10/2005 | Kertesz et al. |
| 2005/0250094 A1 | 11/2005 | Storhoff et al. |
| 2005/0266459 A1 | 12/2005 | Poulsen et al. |
| 2006/0024751 A1 | 2/2006 | May et al. |
| 2006/0030541 A1 | 2/2006 | Garcia et al. |
| 2006/0040293 A1 | 2/2006 | Salonen et al. |
| 2006/0147957 A1 | 7/2006 | Qian et al. |
| 2006/0148846 A1 | 7/2006 | Orwat et al. |
| 2006/0191657 A1 | 8/2006 | Spence et al. |
| 2007/0141583 A1 | 6/2007 | Li et al. |
| 2007/0148657 A1 | 6/2007 | Myerson et al. |
| 2007/0166641 A1 | 7/2007 | Shimizu et al. |
| 2007/0207482 A1* | 9/2007 | Church ................ C12Q 1/6869 435/6.13 |
| 2007/0243545 A1 | 10/2007 | Kilpatrick et al. |
| 2008/0044385 A1 | 2/2008 | Nishi et al. |
| 2008/0050393 A1 | 2/2008 | Tang et al. |
| 2008/0076923 A1 | 3/2008 | Belogi et al. |
| 2008/0096262 A1 | 4/2008 | Kobayashi et al. |
| 2008/0108810 A1 | 5/2008 | Kertesz et al. |
| 2008/0188575 A1 | 8/2008 | Gaspar Martinho et al. |
| 2008/0220451 A1 | 9/2008 | Adler et al. |
| 2008/0227653 A1 | 9/2008 | Fodor et al. |
| 2008/0234474 A1 | 9/2008 | Braman et al. |
| 2008/0269502 A1 | 10/2008 | Gantz et al. |
| 2008/0318226 A1 | 12/2008 | Usui et al. |
| 2009/0123913 A1 | 5/2009 | Barany et al. |
| 2009/0197346 A1 | 8/2009 | Winkler et al. |
| 2009/0221429 A1 | 9/2009 | Fujimoto et al. |
| 2009/0294305 A1 | 12/2009 | Bekki et al. |
| 2010/0047671 A1 | 2/2010 | Chiang et al. |
| 2010/0136542 A1* | 6/2010 | Lee ...................... C12Q 1/6865 435/6.18 |
| 2010/0196902 A1 | 8/2010 | Pestano et al. |
| 2010/0243451 A1* | 9/2010 | Latham ................ C12Q 1/6827 204/452 |
| 2010/0279283 A1 | 11/2010 | Raghunath et al. |
| 2011/0229975 A1 | 9/2011 | Matthiesen et al. |
| 2011/0250698 A1 | 10/2011 | Pollner et al. |
| 2011/0262930 A1 | 10/2011 | Deleersnijder et al. |
| 2011/0281263 A1 | 11/2011 | Matthiesen et al. |
| 2011/0287951 A1 | 11/2011 | Emmert-Buck et al. |
| 2012/0331587 A1 | 12/2012 | Lassen et al. |
| 2013/0017176 A1 | 1/2013 | Hosoda et al. |
| 2013/0040294 A1 | 2/2013 | Matthiesen |
| 2013/0072535 A1 | 3/2013 | Stierli et al. |
| 2013/0156695 A1 | 6/2013 | Sprecher et al. |
| 2013/0230918 A1 | 9/2013 | Wakamiya |
| 2014/0017704 A1 | 1/2014 | Casta et al. |
| 2014/0242589 A1 | 8/2014 | Matthiesen |
| 2017/0283805 A1 | 10/2017 | Bonci et al. |
| 2019/0249235 A1 | 8/2019 | Matthiesen |
| 2020/0232018 A1 | 7/2020 | Matthiesen |
| 2020/0299769 A1 | 9/2020 | Matthiesen |

FOREIGN PATENT DOCUMENTS

| | | |
|---|---|---|
| EP | 1013772 A1 | 6/2000 |
| WO | 9102088 A1 | 2/1991 |
| WO | 9204341 A1 | 3/1992 |
| WO | 9207956 A1 | 5/1992 |
| WO | 9207959 A1 | 5/1992 |
| WO | 1992007956 A1 | 5/1992 |
| WO | 9402638 A1 | 2/1994 |
| WO | 9402639 A1 | 2/1994 |
| WO | 9604000 A1 | 2/1996 |
| WO | 9914226 A2 | 3/1999 |
| WO | 9927103 | 6/1999 |
| WO | 0006773 A1 | 2/2000 |
| WO | 0069899 A1 | 11/2000 |
| WO | 0166804 A2 | 9/2001 |
| WO | 02061137 A2 | 8/2002 |
| WO | 02088396 A2 | 11/2002 |
| WO | 03014398 A2 | 2/2003 |
| WO | 03027328 A2 | 4/2003 |
| WO | 03054209 A2 | 7/2003 |
| WO | 2006007841 A2 | 1/2006 |
| WO | 2006023919 A2 | 3/2006 |
| WO | 2006066039 A2 | 6/2006 |
| WO | 2006093150 A1 | 9/2006 |

(56) References Cited

FOREIGN PATENT DOCUMENTS

| WO | 2006117596 A2 | 11/2006 | |
|---|---|---|---|
| WO | 2007019432 A2 | 2/2007 | |
| WO | 2007019492 A2 | 2/2007 | |
| WO | 2007037314 A1 | 4/2007 | |
| WO | 2007037341 A1 | 4/2007 | |
| WO | 2007058326 A1 | 5/2007 | |
| WO | 2007109441 A2 | 9/2007 | |
| WO | 2007109941 A1 | 10/2007 | |
| WO | 2009074154 A2 | 6/2009 | |
| WO | 2009147537 A2 | 12/2009 | |
| WO | WO 2009/144561 | 12/2009 | |
| WO | 2010097655 A1 | 9/2010 | |
| WO | 2010097707 A1 | 9/2010 | |
| WO | WO 2010/097656 A1 * | 9/2010 | ............... C12Q 1/68 |
| WO | WO 2011/0676678 | 6/2011 | |
| WO | 2011153354 A1 | 12/2011 | |

OTHER PUBLICATIONS

Anonymous, "TOP2A Fish pharmDx kit Code K5333", Dako Product Information, May 24, 2007, 1-33.
Beebe, "Glycerin Antigen Retrieval", Microscopy Today, Issue #99-9, Nov. 1999, 30-31.
Berndt, et al., "Reduced Formamide Content and Hybridization Temperature Results in Increased Non-Radioactive MRNA In Situ Hybridization Signals", Acta Histochemica, vol. 98, No. 1, 1996, 79-87.
Bioprotocols.info, "20X SSC Recipe", Bioprotocols.info, Jul. 28, 2014, 1 page.
Boehringer, et al., "Nucleic Acid Hybridization—General Aspects", Biochemicals Catalog, Chapter III, Jan. 1, 1992, 14-17.
Brown, et al., "Analysis of RNA by Northern and Slot Blot Hybridization", Current Protocols in Molecular Biology, Chapter 4: Unit 4.9, Sep. 2004, 2 pages.
Burke, "Solubility Parameters: Theory and Application", The Book and Paper Group Annual; vol. 3 cool.conservation-us.org [retrieved on Feb. 12, 2014], 1984, 1-33.
Chakrabarti, et al., "The Enhancement of PCR Amplification by Low Molecular Weight Amides", Nucleic Acids Research, vol. 29, No. 11, 2001, 2377-2381.
Chakrabarti, et al., "The enhancement of PCR amplification by low molecular weight sulfones", Nucleic Acids research, vol. 29 No. 11, 2001, 2377-2387.
EPO, "Brief communication—Opposition Proceedings dated Jan. 8, 2018", Application No. 09754209.6, 3 Pages.
Chardonnet, et al., "Human Papillomavirus Detection in Cervical Cells by in Situ Hybridization with Biotinylated Probes", Cytopathology, vol. 3, 1992, 341-350.
Cox, et al., "Fluorescent DNA Hybridization Probe Preparation Using Amine Modification and Reactive Dye Coupling", BioTechniques, vol. 36, No. 1, Jan. 2004, 114-122.
Denny, et al., "Burkitt Lymphoma Cell Line Carrying a Variant Translocation Creates New DNA at the Breakpoint and Violates the Hierarchy of Immunoglobulin Gene Rearrangement", Molecular and Cellular Biology, vol. 5, No. 11, 1985, 3199.
Dow, "Ethylene Glycols", Webpage, Jun. 28, 2012, 3 pages.
Dow, "Propylene Glycols for Industrial Applications", Webpage, Jun. 28, 2012, 4 pages.
EPO, "Acknowledgement of a Document (Opponent) dated Aug. 21, 2018", Application No. 09754209.6, 1 Page.
EPO, "Acknowledgement of a Document (Opponent) dated Feb. 11, 2019", Application No. 12775027.1, 1 Page.
EPO, "Acknowledgement of a Document (Opponent) dated Jul. 1, 2019", Application No. 09754209.6, 1 Page.
EPO, "Acknowledgement of a Document (Opponent) dated Mar. 5, 2019", Application No. 13164094.8, 1 Page.
EPO, "Acknowledgement of a Document (Opponent) dated May 22, 2018", Application No. 13164094.8, 1 Page.
EPO, "Acknowledgement of a Document dated Aug. 21, 2018", Application No. 09754209.6, 1 Page.
EPO, "Acknowledgement of a Document dated Feb. 11, 2019", Application No. 12775027.1, 1 Page.
EPO, "Acknowledgement of a Document dated Jul. 1, 2019", Application No. 09754209.6, 1 Page.
EPO, "Acknowledgement of a Document dated Mar. 5, 2019", Application No. 13164094.8, 1 Page.
EPO, "Acknowledgement of a Document dated May 22, 2018", Application No. 13164094.8, 1 Page.
EPO, "Advice of Delivery dated Aug. 23, 2018", Application No. 09754209.6, 1 Page.
EPO, "Advice of Delivery dated Aug. 24, 2018", Application No. 09754209.6, 1 Page.
EPO, "Advice of Delivery dated Aug. 27, 2018", Application No. 09754209.6, 2 Pages.
EPO, "Advice of Delivery dated Aug. 29, 2018", Application No. 09754209.6, 2 Pages.
EPO, "Advice of Delivery dated Feb. 13, 2019", Application No. 12775027.1, 1 Page.
EPO, "Advice of Delivery dated Feb. 15, 2019", Application No. 12775027.1, 1 Page.
EPO, "Advice of Delivery dated Feb. 26, 2019", Application No. 12775027.1, 1 Page.
EPO, "Advice of Delivery dated Jul. 3, 2019", Application No. 09754209.6, 1 Page.
EPO, "Advice of Delivery dated Jul. 8, 2019", Application No. 09754209.6, 2 Pages.
EPO, "Advice of Delivery dated Mar. 11, 2019", Application No. 13164094.8, 2 Pages.
EPO, "Advice of Delivery dated Mar. 6, 2019", Application No. 13164094.8, 1 Page.
EPO, "Advice of Delivery dated Mar. 8, 2019", Application No. 13164094.8, 1 Page.
EPO, "Advice of Delivery dated Mar. 8, 2019", Application No. 13164094.8, 2 Pages.
EPO, "Advice of Delivery dated May 24, 2018", Application No. 13164094.8, 1 Page.
EPO, "Advice of Delivery dated May 29, 2018", Application No. 13164094.8, 1 Page.
EPO, "Advice of Delivery dated May 29, 2018", Application No. 13164094.8, 2 Pages.
EPO, "Advice of Delivery dated May 30, 2018", Application No. 13164094.8, 2 Pages.
EPO, "Brief Communication—Opposition Proceedings dated Feb. 7, 2018", Application No. 13164094.8, 14 Pages.
EPO, "Brief Communication—Opposition Proceedings dated Jan. 7, 2019", Application No. 13164094.8, 27 Pages.
EPO, "Brief Communication—Opposition Proceedings dated Jul. 1, 2019", Application No. 09754209.6, 15 Pages.
EPO, "Reply of the Patent Proprietor to the Notice(s) of Opposition filed on Sep. 18, 2018", Application No. 12775027.1, 26 pages.
EPO, "Reply of the Patent Proprietor to the Notice(s) of Opposition dated May 17, 2018", Application No. 39754209.6, 67 Pagess.
EPO, "Request for Correction in Reference No. By Opponent filed on Jan. 23, 2018", Application No. 39754209.6, 3 Pages.
EPO, "Request for Documents Pursuant to Rule 83 EPC by Opponent filed on Jan. 2, 2018", Application No. 39754209.6, 3 Pages.
EPO, "Request for Interpreters by Opponent filed on Mar. 5, 2019", Application No. 09754209.6, 1 Page.
EPO, "Response to Brief Communication dated Jan. 8, 2018 & Further to Notice of Opposition by Opponent filed on Jan. 26, 2018", Application No. 09754209.6, 4 Pages.
EPO, "Response to the Opponent's Letter dated Feb. 1, 2018 filed on May 17, 2018", Application No. 13164094.8, 15 Pages.
EPO, "Summons to Attend Oral Proceedings dated Aug. 21, 2018", Application No. 09754209.6, 22 Pages.
EPO, "Summons to Attend Oral Proceedings dated Feb. 11, 2019", Application No. 12775027.1, 7 Pages.
EPO, "Summons to Attend Oral Proceedings dated May 22, 2018", Application No. 13164094.8, 37 Pages.
EPO, "Summons to Attend Oral Proceedings Received by Opponent dated Aug. 21, 2018", Application No. 39754209.6, 22 Pages.

(56) References Cited

OTHER PUBLICATIONS

EPO, "Summons to Attend Oral Proceedings Received by Opponent dated Feb. 11, 2019", Application No. 12775027.1, 7 Pages.
EPO, "Summons to Attend Oral Proceedings Received by Opponent dated May 22, 2018", Application No. 13164094.8, 37 Pages.
EPO, "Written Submission by Opponent in Preparation to/during Oral Proceedings filed on Apr. 27, 2019", Application No. 09754209.6, 17 Pages.
EPO, "Written Submission by Opponent in Preparation to/during Oral Proceedings filed on Nov. 7, 2018", Application No. 13164094.8, 7 Pages.
EPO, "Written Submission by Opponent in Preparation to/during Oral Proceedings filed on Sep. 28, 2018", Application No. 13164094.8, 9 Pages.
EPO, "Written Submission by Opponent in Preparation to/during Oral Proceedings dated Mar. 7, 2019", Application No. 09754209.6, 14 Pages.
EPO, "Written Submission in Preparation to/during Oral Proceedings filed on Mar. 5, 2019", Application No. 39754209.6, 84 Pages.
EPO, "Written Submission in Preparation to/during Oral Proceedings filed on Nov. 22, 2018", Application No. 13164094.8, 123 Pages.
EPO, "Written Submission in Preparation to/during Oral Proceedings filed on Sep. 27, 2018", Application No. 13164094.8, 76 Pages.
Hansen, "Excerpt Print Version: Hansen Solubility Parameters, a User's Handbook", 2nd Edition, 2007, 546 pages.
Hayat, et al., "Factors Affecting Antigen Retrieval", Chapter 4 of Microscopy, Immunohistochemistry and Antigen Retrieval, New York, 2002, 71-93.
Hitzeman, et al., "Dextran Sulfate as a Contaminant of DNA Extracted from Concentrated Viruses and as an Inhibitor of DNA Polymerases", Journal of Virology, vol. 27, No. 1, Jul. 1978, 255-257.
Huber, et al., "Detection of Partial Denaturation in AT-Rich DNA Fragments by Ion-Pair Reserved-Phase Chromatography", Analytical Chemistry, vol. 68, No. 17, Sep. 1, 1996, 2959-2965.
Invitrogen, "Superscript™ First-Strand Synthesis System for RT-PCR", Invitrogen by Life Technologies, Mar. 5, 2007, 1 pages.
Invitrogen™, "Denhardt's Solution (50X)", Catalog number: 750018, ThermoFisher Scientific, 2007, 2 pages.
IUPAC Gold Book, "Glycols", Compendium of Chemical Terminology, 2nd ed. (the "Gold Book"). Compiled by A.D. McNaught and A. Wilkinson. Blackwell Scientific Publications, Oxford (1997), 1997, 1 page.
IUPAC Gold Book, "Solution", Compendium of Chemical Terminology, 2nd ed. (the "Gold Book"). Compiled by A. D. McNaught and A. Wilkinson. Blackwell Scientific Publications, Oxford (1997), 2 pages.
Kaye & Laby, "3.7.1 Dipole moments and dipole lengths", NPL(National Physical Laboratory) Kaye & Laby Tables of Physical & Chemical Constants, Mar. 23, 2008, 1-2.
Kiyama, et al., "In Situ Hybridization Method", New Genetic Engineering Handbook, Experimental Medical Edition, Muramatsu Masami, et al. Editors, Apr. 20, 1996, 202-203.
Kurreck, "Improvement Through Novel Chemical Modifications", Antisense technologies, Eur. J. Biochem., vol. 270, 2003, 1628-1644.
Launay, et al., "Hansen solubility parameters for a carbon fiber/epoxy composite", Carbon, vol. 45, No. 2859, 2007.
Lawson, et al., "Dimethyl formamide-free, urea-NaCl fluorescence in situ hybridization assay for *Staphylococcus aureus*", Letters in Applied Microbiology, vol. 54, No. 263, 2011.
Luo, et al. "Establishment of a Simple and Useful Way for Preimplantation Genetic Diagnosis of Chromosomal Diseases", Journal of Huazhong University of Science and Technology, [Med Sci], vol. 27, No. 3, 2007, 315-317.
Lyondellbasell, "N-Methy-2-Pyrrolidone", Application Data [retrieved on Mar. 7, 2013], 4 pages.
Lyondellbasell, "Products & Technology", Webpage, Mar. 7, 2013, 1 page.

Ma, et al., "Optimization of Hybridization Efficiency in cDNA Chip Technology", 2002, 153-157.
Markarian, et al., "Effect of Diethylsulfoxide on the Thermal Denaturation of DNA", Biopolymers, vol. 82, No. 1, May 2006, 1-5.
Matthiesen, et al., "Fast and Non-Toxic in Situ Hybridization without Blocking of Repetitive Sequences", PLOS One, vol. 7, No. 7, Jul. 2012, e40675.
McAllister, et al., "In situ Hybridization to Study the Origin and Fate of Identified Neurons", Science, vol. 222, No. 300, 1983, 800-808.
Mochizuki, et al., "Solvent Effect on PCR From a Viewpoint of a Change of Microscopic Environment of Mg(2+) in a Solution", Biochem. Biophys. Res. Commun., Jun. 6, 2007, 1 page.
Moroni, et al., "Gene Copy Number For Epidermal Growth Factor Receptor (EGFR) and Clinical Response to AntiEGFR Treatment in Colorectal Cancer: A Cohort Study", Lancet Oncology, vol. 6, May 2005, 279-286.
Nielsen, et al., "PNA Suppression Method Combined with Fluorescence in Situ Hybridization (FISH) Technique", Chapter 10 of PRINS and PNA Technologies in Chromosomal Investigation (Ed. Franck Pellestor), 2006, 22 pages.
Olsen, et al., "Amplification of HER2 and TOP2A and Deletion of TOP2A Genes in Breast Cancer Investigated by New Fish Probes", Acta Oncologica, vol. 43, No. 1, 2004, 34-42.
PCT, "International Search Report and Written Opinion dated Apr. 28, 2010", Application No. PCT/IB2009/007917, 10 pages.
PCT, "International Search Report and Written Opinion dated Feb. 15, 2010", Application No. PCT/IB2009/006548, 9 pages.
PCT, "International Search Report and Written Opinion dated Jul. 12, 2010", Application No. PCT/IB2010/000659, 11 pages.
PCT, "International Search Report and Written Opinion dated May 7, 2010", Application No. PCT/IB2009/007725, 12 pages.
PCT, "International Search Report and Written Opinion dated Sep. 22, 2009", Application No. PCT/IB2009/005893, 9 pages.
PCT, "International Search Report dated Jan. 14, 2013", International Application No. PCT/IB2012/002359, 4 pages.
EPO, "Brief Communication—Opposition Proceedings dated Mar. 11, 2019", Application No. 09754209.6, 2 Pages.
EPO, "Brief Communication—Opposition Proceedings dated Mar. 11, 2019", Application No. 09754209.6, 83 Pages.
EPO, "Brief Communication—Opposition Proceedings dated Mar. 13, 2019", Application No. 09754209.6, 23 Pages.
EPO, "Brief Communication—Opposition Proceedings dated May 2, 2018", Application No. 09754209.6, 4 Pages.
EPO, "Brief Communication—Opposition Proceedings dated May 25, 2018", Application No. 13164094.8, 16 Pages.
EPO, "Brief Communication—Opposition Proceedings dated May 25, 2018", Application No. 09754209.6, 64 Pages.
EPO, "Brief Communication—Opposition Proceedings dated May 3, 2019", Application No. 09754209.6, 51 Pages.
EPO, "Brief Communication—Opposition Proceedings dated Nov. 13, 2018", Application No. 13164094.8, 6 Pages.
EPO, "Brief Communication—Opposition Proceedings dated Nov. 30, 2018", Application No. 13164094.8, 126 Pages.
EPO, "Brief Communication—Opposition Proceedings dated Oct. 16, 2017", Application No. 13164094.8, 67 Pages.
EPO, "Brief Communication—Opposition Proceedings dated Oct. 2, 2018", Application No. 12775027.1, 27 Pages.
EPO, "Brief Communication—Opposition Proceedings dated Oct. 5, 2018", Application No. 13164094.8, 77 Pages.
EPO, "Brief Communication—Opposition Proceedings dated Oct. 5, 2018", Application No. 13164094.8, 8 Pages.
EPO, "Brief Communication dated Jan. 8, 2018 of the EPO in the Opposition Proceedings Including the Aforementioned Document D14 (Termed "D5" in the Examination and Opposition Proceedings of EP 2285979) dated Feb. 7, 2018", Patent No. EP 2285979, 1 page.
EPO, "Communication of a Notice of Opposition—First Information to Patent Proprietor dated Apr. 24, 2018", Application No. 12775027.1, 1 Page.
EPO, "Communication of a Notice of Opposition—First Information to Patent Proprietor dated Apr. 26, 2017", Application No. 13164094.8, 1 Page.

(56) References Cited

OTHER PUBLICATIONS

EPO, "Communication of a Notice of Opposition—First Information to Patent Proprietor dated Oct. 20, 2017", Application No. 09754209.6, 1 Page.
EPO, "Communication of Further Notices of Opposition Pursuant to Rule 79(2) EPC dated Jan. 15, 2018", Application No. 09754209.6, 1 Page.
EPO, "Communication of Further Notices of Opposition Pursuant to Rule 79(2) EPC dated May 30, 2017", Application No. 13164094.8, 1 Page.
EPO, "Communication of Further Notices of Opposition Pursuant to Rule 79(2) EPC dated May 8, 2018", Application No. 12775027.1, 1 Page.
EPO, "Communication of Notices of Opposition (R. 79(1) EPC) dated Jan. 15, 2018", Application No. 09754209.6, 1 Page.
EPO, "Communication of Notices of Opposition (R. 79(1) EPC) dated May 30, 2017", Application No. 13164094.8, 1 Page.
EPO, "Communication of Notices of Opposition (R. 79(1) EPC) dated May 8, 2018", Application No. 12775027.1, 1 Page.
EPO, "Communication Pursuant to Rule 82(2) EPC to Pay Printing Fees and File Translations dated Jul. 24, 2019", Application No. 13164094.8, 6 Pages.
EPO, "Communication to Opponent Concerning Maintenance dated Jul. 24, 2019", Application No. 13164094.8, 4 Pages.
EPO, "Electronic Versions of the Handwritten Amendments (Written Submission) submitted on Dec. 19, 2018", Application No. 13164094.8, 26 Pages.
EPO, "Electronic Versions of the Handwritten Amendments submitted on May 31, 2019", Application No. 09754209.6, 14 Pages.
EPO, "EPO Request for Documents Pursuant Rule 83 EPC/ Request for Translation Pursuant Rule 3(3) EPC to opponent dated Oct. 20, 2017", Application No. 09754209.6, 1 Page.
EPO, "Extended European Search Report dated Aug. 14, 2013", Application No. 13164099.7, 5 pages.
EPO, "Extended European Search Report dated Aug. 8, 2013", Application No. 13164094.8, 5 pages.
EPO, "Extended European Search Report dated Jun. 6, 2018", Application No. 18165184.5, 8 pages.
EPO, "Information About the Result of Oral Proceedings dated May 7, 2019", Application No. 09754209.6, 10 Pages.
EPO, "Information About the Result of Oral Proceedings dated Nov. 30, 2018", Application No. 13164094.8, 6 Pages.
EPO, "Interlocutory Decision in Opposition Proceedings (Art. 101(3)(a) and 106(2) EPC) dated Jul. 1, 2019", Application No. 09754209.6, 66 Pages.
EPO, "Interlocutory Decision in Opposition Proceedings (Art. 101(3)(a) and 106(2) EPC) dated Mar. 5, 2019", Application No. 13164094.8, 40 Pages.
EPO, "Internal Form—Opposition/Addressees dated Jul. 1, 2019", Application No. 09754209.6, 2 Pages.
EPO, "Internal Form—Opposition/Addressees dated Mar. 5, 2019", Application No. 13164094.8, 2 Pages.
EPO, "Maintenance of the Patent With the Documents Specified in the Final Decision dated Jul. 17, 2019", Application No. 13164094.8, 1 Page.
EPO, "Minutes of the Oral Proceedings (Opposition Division)—Conclusion of the Proceedings dated Mar. 5, 2019", Application No. 13164094.8, 3 Pages.
EPO, "Notice of Opposition by Opponent filed on Apr. 18, 2018", Application No. 12775027.1, 34 Pages.
EPO, "Notice of Opposition by Opponent filed on Oct. 11, 2017", Application No. 09754209.6, 31 Pages.
EPO, "Notice of Opposition Filed by Opponent filed on Apr. 20, 2017", Application No. 13164094.8, 37 Pages.
EPO, "Oppodrex with Handwritten Amendments", Application No. 09754209.6, 39 Pages.
EPO, "Oppodrex with Handwritten Amendments dated Mar. 5, 2019", Application No. 13164094.8, 50 Pages.
EPO, "Patentee's Letter of Oct. 15, 2015 in the Examination Proceedings", Application No. 12775027.1, 7 pages.
EPO, "Provision of the Minutes in Accordance with Rule 124(4) EPC dated Jul. 1, 2019", Application No. 09754209.6, 21 Pages.
EPO, "Provision of the Minutes in Accordance with Rule 124(4) EPC dated Mar. 5, 2019", Application No. 13164094.8, 25 Pages.
EPO, "Reply from the Opponent to Submission of Proprietor filed on Feb. 1, 2018", Application No. 13164094.8, 13 Pages.
EPO, "Reply of the Patent Proprietor to the Notice(s) of Opposition filed on Oct. 6, 2017", Application No. 13164094.8, 66 Pages.
PCT, "International Search Report dated Jun. 16, 2008", Application No. PCT/DK2008/000066, 3 pages.
Powell, et al., "Metallographic in Situ Hybridization", Progress in Pathology, Human Pathology, vol. 38, 2007, 1145-1159.
Rigby, et al., "Fluorescence in Situ Hybridization with Peptide Nucleic Acid Probes for Rapid Identifications of Candida Albicans Directly from Blood Culture Bottles", Journal of Clinical Microbiology, vol. 4, No. 6, Jun. 2002, 2182-2186.
Wahl, et al., "Efficient Transfer of Large DNA Fragments From Agarose Gels to Diazobenzyloxymethyl-Paper and Rapid Hybridization by Using Dextran Sulfate", Proc. Natl. Acad. Sci. USA. Biochemistry, vol. 76, No. 8, Aug. 1979, 3683-3687.
Sassoon, et al., "Detection of Messenger RNA by in Situ Hybridization", Methods in Enzymology, vol. 225, No. 384, 1993, 384-404.
Shapiro, et al., "Detection of N-myc Gene Amplification by Fluorescence in Situ Hybridization", Diagnostic Utility for Neuroblastoma, American Journal of Pathology, vol. 142, No. 5, May 1993, 1339-1346.
Xi, et al., "Use of DNA and Peptide Nucleic Acid Molecular Beacons for Detection and Quantification of rRNA in Solution and in Whole Cells", Applied and Environmental Microbiology, vol. 69, No. 9, Sep. 2003, 5673-5678.
Stender, et al., "Fluorescence in Situ Hybridization Assay Using Peptide Nucleic Acid Probes for Differentiation between Tuberculous and Nontuberculous Mycobacterium Species in Smears of Mycobacterium Cultures", Journal of Clinical Microbiology, vol. 37, No. 9, Sep. 1999, 2760-2765.
Stratagene, "Gene Characterization Kits", Stratagene Catalogue, 1988, p. 39.
Stratagene, "The Stratagene Catalog", 1988, p. 39.
Summersgill, et al., "Fluorescence and Chromogenic in Situ Hybridization to Detect Genetic Aberrations in Formalin-Fixed Paraffin Embedded Material, Including Tissue Microarrays", Nature Protocols, vol. 3, No. 2, Jan. 2008, 220-234.
The European Agency for the Eval, "2-Pyrrolidone", Summary Report, Committee for Veterinary Medical Products, Retrieved from the Internet: <URL: www.ema.europa.eu/docs/en_GB/document_library/Maximum_Residue_Limits_-_Report/2009/11/WC500015798.pdf>, Jul. 1998, 5 pages.
Tkachuk, et al., "Detection of bcr-abl Fusion in Chronic Myelogeneous Leukemia by in Situ Hybridization", Science, vol. 250, Issue 4980, Oct. 26, 1990, 559-562.
Toyozo, et al., "Principal Assay Method in Infection Diagnosis", Chapter 3. Diagnosis of Infection by DNA Probe, Applied DNA Probe Technology, Feb. 5, 1988, 36-39.
Tsuruoka, et al., "Rapid Hybridization at High Salt Concentration and Detection of Bacterial Dna Using Fluorescence Polarization", Combinatorial Chemistry & High Throughput Screening, vol. 6, No. 3, 2003, 225-234.
Woenckhaus, et al., "Multitarget FISH and LOH Analyses at Chromosome 3p in Non-Small Cell Lung Cancer and Adjacent Bronchial Epithelium", Am. J. of Clin. Pathol., vol. 123, No. 5, 2005, 752-761.
Wilkinson, et al., "Detection of Messenger RNA by in Situ Hybridization to Tissue Sections and Whole Mounts", Methods in Enzymology, vol. 225, No. 361, 1993.
Wikipedia, "Solvent", Wikipedia, Apr. 17, 2019, 15 pages.
Wikipedia, "2-Pyrrolidone", Webpage, Nov. 1, 2012, 3 pages.
Webpage, "OPTIM Synthetic Glycerine—Vapor Pressure and Boiling Point", Webpage, Jun. 28, 2007, 1 page.
Wang, "Simultaneous Detection and Differentiation of *Staphylococcus* Species in Blood Cultures Using Fluorescence in situ Hybridization", Medical Principles and Practice, vol. 19, No. 218, 2010, 4 pages.

(56) References Cited

OTHER PUBLICATIONS

EPO, "Brief Communication—Opposition Proceedings dated Sep. 6, 2019", Application No. 12775027.1, 2 Pages.
EPO, "Brief Communication—Opposition Proceedings dated Sep. 9, 2019", Application No. 12775027.1, 2 Pages.
EPO, "Brief Communication—Opposition Proceedings dated Sep. 12, 2019", Application No. 12775027.1, 6 Pages.
EPO, "Brief Communication—Opposition Proceedings dated Sep. 16, 2019", Application No. 12775027.1, 1 Page.
EPO, "Request for Correction in Minutes of Oral Proceedings filed on Aug. 21, 2019", Application No. 09754209.6, 3 Pages.
EPO, "Request for Interpreters by Opponent filed on Sep. 2, 2019", Application No. 12775027.1, 3 Pages.
EPO, "Request for Interpreters filed on Sep. 2, 2019", Application No. 12775027.1, 1 Page.
EPO, "Written Submission by Opponent in Preparation to/during Oral Proceedings Filed on Sep. 4, 2019", Application No. 12775027.1, 6 Pages.
EPO, "Written Submission in Preparation to/during Oral Proceedings Filed on Sep. 4, 2019", Application No. 12775027.1, 107 Pages.
Brief Communication regarding Letter from Proprietor of Aug. 21, 2019—Opposition Proceedings dated Oct. 1, 2019, Application No. 09754209.6, 7 Pages.
Communication of Bibliographic Data dated Oct. 28, 2019, Application No. 09754209.6, 2 Pages.
Communication Pursuant to Rule 82(2) that Interlocutory Decision has become Final. dated Oct. 28, 2019, Application No. 09754209.6, 2 Pages.
Decision revoking the European patent dated Nov. 29, 2019, Application No. 12775027.1, 46 Pages.
Decision to maintain European Patent. No. 2636756 dated Oct. 24, 2019, Application No. 13164094.8, 1 Page.
Information About the Result of Oral Proceedings dated Nov. 4, 2019, Application No. 12775027.1, 9 Pages.
Maintenance of the Patent with the Documents Specified in the Final Decision dated Oct. 17, 2019, Application No. 09754209.6, 1 Page.
Proprietor's Response to Communication Pursuant to Rule 82(2) EPC Filed on Oct. 11, 2019, Application No. 13164094.8, 19 pages.
Termination of the Opposition Proceedings with Maintenance of Patent dated Oct. 18, 2019, Application No. 13164094.8, 1 Page.
Written Submission by Opponent in Preparation to/during Oral Proceedings Filed on Oct. 30, 2019, Application No. 12775027.1, 10 Pages.
Massey, et al., "A Fluorescent Molecular Switch for Room Temperature Operation Based on Oligonucleotide Hybridization Without Labeling of Probes or Targets", Analytica Chimica Acta, vol. 750, 2012, 182-190.
Winship, "An Improved Method For Directly Sequencing PCR Amplified Material Using Dimethyl Sulphoxide", Nucleic Acids Research, vol. 17, No. 3, 1989, 1266.
Gelfand, et al., "Thermostable DNA Polymerases", PCR Protocols: A Guide to Methods and Applications, Part One. Basic Methodology, 1990, 129-141.
Pernthaler, et al., "Fluorescence In Situ Hybridization (FISH) With rRNA-Targeted Oligonucleotide Probes", Methods in Microbiology vol. 30—Abstract Only, 2000, 207-210.
Powell, et al., "Rapid Confirmation of Single Copy Lambda Prophage Integration By PCR", Nucleic Acids Research, vol. 22, No. 25, 1994, 5765-5766.
Extended European Search Report dated Aug. 19, 2020, Application No. 20167307.6, 7 pages.
Auxiliary Request 1 filed by Patentee dated Dec. 18, 2020, EP Application No. 15184389.3, 12 pages.
Auxiliary Request 2 filed by Patentee dated Dec. 18, 2020, EP Application No. 15184389.3, 12 pages.
Auxiliary Request 3 iled by Patentee dated Dec. 18, 2020, EP Application No. 15184389.3, 12 pages.
Auxiliary Request 4 filed by Patentee dated Dec. 18, 2020, EP Application No. 15184389.3, 12 pages.
Auxiliary Request 5 filed by Patentee dated Dec. 18, 2020, EP Application No. 15184389.3, 12 pages.
Patentee Response to Opposition filed on Dec. 18, 2020, EP Application No. 15184389.3, 45 pages.
Main Request filed by Patentee dated Dec. 18, 2020, EP Application No. 15184389.3, 12 pages.
Communication Re: Patentee Response to Opposition dated Jan. 11, 2021, EP Application No. 15184389.3, 47 pages.
Polyethylene glycol mono(4-tert-octylphenyl) ether. CAS Common Chemistry. CAS, a division of the American Chemical Society, n.d. https://commonchemistry.cas.org/detail?ref=9002-93-1 (retrieved Mar. 26, 2021) (CAS RN: 9002-93-1), 4 pages.
Polyoxyethylene sorbitan monolaurate. CAS Common Chemistry. CAS, a division of the American Chemical Society, n.d. https://commonchemistry.cas.org/detail?ref=9005-64-5 (retrieved Mar. 26, 2021) (CAS RN: 9005-64-5), 5 pages.
Response to Patentee's Submission (dated Dec. 18, 2020) filed on Apr. 1, 2021, EP Application No. 15184389.3, 19 pages.
Summons to Oral Proceedings pursuant to Rule 115(1) EPC dated Apr. 8, 2021, EP Application No. 15184389.3, 25 Pages.
Polysorbate 20. (n.d.). In Wikipedia, last edited Feb. 17, 2021, https://en.wikipedia.org/wiki/Polysorbate_20, 3 pages.
Triton X-100. (n.d.). In Wikipedia, last edited Mar. 12, 2021, https://en.wikipedia.org/wiki/Triton_X-100, 4 pages.

* cited by examiner

HYBRIDIZATION COMPOSITIONS AND METHODS

CROSS REFERENCES TO RELATED APPLICATION

This application is a national stage filing under 35 U.S.C. § 371 of International Application No. PCT/EP2012/070877, filed Oct. 22, 2012, in English and designating the United States of America, which is based on and claims the benefit of priority from U.S. Provisional Application No. 61/550,016, filed Oct. 21, 2011, all of which are incorporated herein by reference.

FIELD OF THE INVENTION

The present invention relates to compositions and methods for use in hybridization applications. The present invention also relates to compositions and methods for example, for use in in situ hybridization (ISH) applications. In one embodiment, the present invention involves molecular examination of DNA (deoxyribonucleic acid) and RNA (ribonucleic acid). In particular, the invention can be used for the molecular examination of DNA and RNA in the fields of cytology, histology, and molecular biology. In other embodiments, the present invention relates to the energy (e.g., incubation time and heat) required during hybridization between nucleic acids, e.g., in in situ hybridization targeting DNA and RNA.

BACKGROUND AND DESCRIPTION

Double stranded nucleic acid molecules (i.e., DNA, DNA/RNA and RNA/RNA) associate in a double helical configuration. This double helix structure is stabilized by hydrogen bonding between bases on opposite strands when bases are paired in one particular way (A+T/U or G+C) and hydrophobic bonding among the stacked bases. Complementary base paring (hybridization) is central to all processes involving nucleic acid.

In a basic example of hybridization, nucleic acid probes or primers are designed to bind, or "hybridize," with a target nucleic acid, for example, DNA or RNA in a sample. One type of hybridization application, in situ hybridization (ISH), includes hybridization to a target in a specimen wherein the specimen may be in vivo, in vitro, in situ, or for example, fixed or adhered to a glass slide. The probes may be labeled to make identification of the probe-target hybrid possible by use of a fluorescence or bright field microscope/scanner. Such labeled probes can be used, for example, to detect genetic abnormalities in a target sequence, providing valuable information about, e.g., prenatal disorders, cancer, and other genetic or infectious diseases.

The efficiency and accuracy of nucleic acid hybridization assays mostly depend on at least one of three major factors: a) denaturation (i.e., separation of, e.g., two nucleic acid strands) conditions, b) renaturation (i.e., re-annealing of, e.g., two nucleic acid strands) conditions, and c) post-hybridization washing conditions.

In order for the probes or primers to bind to the target nucleic acid in the sample, complementary strands of nucleic acid may be separated. This strand separation step, termed "denaturation," typically requires aggressive conditions to disrupt the hydrogen and hydrophobic bonds in the double helix. Once the complementary strands of nucleic acid have been separated, a "renaturation" or "reannealing" step allows the primers or probes to bind to the target nucleic acid in the sample. This step is also sometimes referred to as the "hybridization" step.

Traditional hybridization experiments, such as ISH assays, use high temperatures (e.g., 95° C. to 100° C.) and/or high concentration formamide-containing solutions (e.g., greater than 40%) to denature doubled stranded nucleic acid. However, these methods have significant drawbacks.

For example, heat can be destructive to the structure of the nucleic acid itself because the phosphodiester bonds may be broken at high temperatures, leading to a collection of broken single stranded nucleic acids. In addition, heat can lead to complications when small volumes are used, since evaporation of aqueous buffers is difficult to control.

Formamide is a solvent that has a destabilizing effect on the helical state of, for example, DNA, RNA, and analogs by displacing loosely and uniformly bound hydrate molecules and by causing "formamidation" of the Watson-Crick binding sites. Thus, formamide has a destabilizing effect on double stranded nucleic acids and analogs, allowing denaturation to occur at lower temperatures. However, although formamide lowers the melting temperature (Tm) of double-stranded nucleic acid, when used at high concentrations, it also significantly prolongs the renaturation time, as compared to aqueous denaturation solutions without formamide.

In addition, using formamide has disadvantages beyond a long processing time. Formamide is a toxic, hazardous material, subject to strict regulations for use and waste. Furthermore, the use of of formamide appears to cause morphological destruction of cellular, nuclear, and/or chromosomal structure.

Moreover, the use of formamide, while accepted as the standard technique for hybridization, is hampered by the long time required to complete the hybridization, depending on the conditions and the nucleic acid fragments or sequences used. For example, the denaturation step is followed by a longer time-consuming hybridization step, which, e.g., in a traditional fluorescent in situ hybridization (FISH) protocol takes 14-24 hours, and can even take up to 72 hours. Examples of traditional hybridization times are shown in FIGS. 1 and 2.

The step of re-annealing (i.e., hybridizing) two complementary strands of nucleic acid chains is by far the most time-consuming aspect of an assay using hybridization. Until now it was believed that the use of chaotropic agents, such as formamide, guanidinium hydrogen, and urea, which interfere with the Watson-Crick binding sites of nucleic acid bases and thereby disturb the hydrogen bonds between complementary nucleic acid bases, was one way to lower the melting temperature (Tm) of the complementary chains. However, although the use of chaotropic agents lowers the Tm, these agents appear to significantly prolong the hybridization time compared to hybridization in an aqueous solution without a chaotropic agent. Furthermore, besides the disadvantage of the long processing time, the use of formamide appears to incur morphological destruction of cellular, nuclear, and/or chromosomal structure. Finally, formamide is considered a toxic and hazardous chemical to humans.

In some embodiments, the present invention provides several potential advantages over prior art hybridization applications, such as faster hybridization times, lower hybridization temperatures, and less toxic hybridization solvents.

SUMMARY OF THE INVENTION

It is an object of the present invention to provide methods and compositions which result in hybridization applications having at least one of the following advantages: highly sensitive, technically easy, flexible and reliable hybridization procedures, and fast analyses. In some embodiments, for example, one advantage may be the ability to tailor the hybridization time by varying the temperature of the hybridization reaction to a much greater degree than is available using prior art methods. For example, hybridization may be possible at room temperature.

In one embodiment, the compositions and methods of the invention lower the energy necessary for hybridization. The compositions and methods of the invention are applicable to any hybridization technique. The compositions and methods of the invention are also applicable to any molecular system that hybridizes or binds using base pairing, such as, for example, DNA, RNA, a peptide nucleic acid (PNA) or locked nucleic acid (LNA), and synthetic and natural analogs thereof.

The nucleic acid hybridization method and compositions of the present invention may be used for the in vivo or in vitro analysis of genomic DNA, chromosomes, chromosome fragments, genes, and chromosome aberrations such as translocations, deletions, amplifications, insertions, mutations, or inversions associated with a normal condition or a disease. Further, the methods and compositions are useful for detection of infectious agents as well as changes in levels of expression of RNA, e.g., messenger RNA (mRNA) and its complementary DNA (cDNA).

Other uses include the in vivo, in vitro, or in situ analysis of mRNA, viral RNA, viral DNA, small interfering RNA (siRNA), small nuclear RNA (snRNA), non-coding RNA (ncRNA, e.g., tRNA and rRNA), transfer messenger RNA (tmRNA), micro RNA (miRNA), piwi-interacting RNA (piRNA), long noncoding RNA, small nucleolar RNA (snoRNA), antisense RNA, double-stranded RNA (dsRNA), methylations and other base modifications, single nucleotide polymorphisms (SNPs), copy number variations (CNVs), and nucleic acids labeled with, e.g., radioisotopes, fluorescent molecules, biotin, 2,4-dinitrophenol (DNP), digoxigenin (DIG), or antigens, alone or in combination with unlabeled nucleic acids.

The nucleic acid hybridization method and compositions of the present invention are useful for in vivo, in vitro, or in situ analysis of nucleic acids using techniques such as northern blot, Southern blot, flow cytometry, autoradiography, fluorescence microscopy, chemiluminescence, immunohistochemistry, virtual karyotype, gene assay, DNA microarray (e.g., array comparative genomic hybridization (array CGH)), gene expression profiling, Gene ID, Tiling array, gel electrophoresis, capillary electrophoresis, and in situ hybridizations such as FISH, SISH, CISH.

In one embodiment, the methods and compositions of the invention are useful for nucleic acid hybridization applications, with the proviso that such applications do not include amplification of the nucleic acid such as, e.g., by polymerase chain reaction (PCR), in situ PCR, etc.

The methods and compositions of the invention may be used on in vitro and in vivo samples such as bone marrow smears, blood smears, paraffin embedded tissue preparations, enzymatically dissociated tissue samples, bone marrow, amniocytes, cytospin preparations, imprints, etc.

In one embodiment, the invention provides methods and compositions for hybridizing at least one molecule to a target. The invention may, for example, reduce the dependence on formamide. For example, the methods and compositions of the invention may lower the energy barrier to hybridization using cyclic and/or non-cyclic solvents. The lower energy barrier may reduce the time and or temperature necessary for hybridization. Thus, in some aspects, the present invention overcomes a major time consuming step in hybridization assays.

One aspect of the invention is a composition or solution for use in hybridization applications. Compositions for use in the invention include an aqueous composition comprising at least one nucleic acid sequence and at least one solvent in an amount effective to denature double-stranded nucleotide sequences. In certain embodiments, the solvent is chosen from N,N-dimethyl-acetamide, isobutyramide, tetramethylene sulfoxide, and 1,3-dimethyl-3,4,5,6-tetrahydro-2(1H)-pyrimidinone. In other embodiments, the solvent is non-cyclic.

According to yet another aspect, the invention discloses a method of hybridizing nucleic acid sequences comprising:
  providing a first nucleic acid sequence,
  providing a second nucleic acid sequence,
  providing a hybridization composition comprising at least one solvent in an amount effective to denature double-stranded nucleotide sequences, and
  combining the first and the second nucleic acid sequence and the hybridization composition for at least a time period sufficient to hybridize the first and second nucleic acid sequences,
  wherein the solvent is chosen from butadiene sulfone, tetrahydrothiophene 1-oxide (tetramethylene sulfoxide), d-valerolactam (2-piperidone), 2-pyrrolidone, cyclopentanone, N-methyl-2-pyrrolidone, 1,3-dimethyl-3,4,5,6-tetrahydro-2(1H)-pyrimidinone, N,N-dimethyl-acetamide and isobutyramide.

The method may, for example, comprise:
  providing a first nucleic acid sequence, and
  applying a hybridization composition comprising a second nucleic acid sequence and a solvent in an amount effective to denature double stranded nucleotide sequences to said first nucleic acid sequence for at least a time period sufficient to hybridize the first and second nucleic acid sequences,
wherein the solvent is chosen from butadiene sulfone, tetrahydrothiophene 1-oxide (tetramethylene sulfoxide), d-valerolactam (2-piperidone), 2-pyrrolidone, cyclopentanone, N-methyl-2-pyrrolidone, 1,3-dimethyl-3,4,5,6-tetrahydro-2(1H)-pyrimidinone, N,N-dimethyl-acetamide and isobutyramide.

In one embodiment, the first nucleic acid sequence is in a biological sample. In another embodiment, the biological sample is a cytology or histology sample.

In one embodiment, the first nucleic acid sequence is a single stranded sequence and the second nucleic acid sequence is a double stranded sequence. In another embodiment, the first nucleic acid sequence is a double stranded sequence in a biological sample and the second nucleic acid sequence is a single stranded sequence. In yet another embodiment, both the first and second nucleic acid sequences are double stranded. In yet another embodiment, both the first and second nucleic acid sequences are single stranded.

In one embodiment, a sufficient amount of energy to hybridize the first and second nucleic acids is provided.

In one embodiment, the hybridization of the first nucleic acid sequence to the second nucleic acid sequence occurs in less than 2 hours, such as, for example, less than 1 hour.

According to yet another aspect of the present invention, the hybridization energy is provided by heating the hybridization composition and nucleic acid sequence. Thus, the step of hybridizing may include the steps of heating and cooling the hybridization composition and nucleic acid sequences.

According to another aspect of the invention, the denaturation and hybridization steps may occur separately. For example, the specimen may be denatured with a solution without probe and thereafter hybridized with probe.

A further aspect of the invention comprises a method wherein the step of providing a sufficient amount of energy to hybridize the nucleic acids involves a heating step performed by the use of microwaves, hot baths, hot plates, heat wire, peltier element, induction heating, or heat lamps.

According to another aspect the present invention relates to a method wherein the hybridization takes less than 4 hours. In some embodiments, the hybridization takes less than 2 hours. In other embodiments, the hybridization takes less than 1 hour. In other embodiments, the hybridization takes less than 30 minutes. In still other embodiments, the hybridization takes less than 15 minutes. In other embodiments, the hybridization takes less than 5 minutes.

According to a further aspect, the invention relates to the use of a composition comprising at least one nucleic acid sequence and at least one solvent in an amount effective to denature double-stranded nucleotide sequences in hybridization assays. In certain embodiments, the solvent is chosen from butadiene sulfone, tetrahydrothiophene 1-oxide (tetramethylene sulfoxide), d-valerolactam (2-piperidone), 2-pyrrolidone, cyclopentanone, N-methyl-2-pyrrolidone, 1,3-dimethyl-3,4,5,6-tetrahydro-2(1H)-pyrimidinone, N,N-dimethyl-acetamide and isobutyramide.

In certain embodiments, the solvent is chosen from N,N-dimethyl-acetamide, isobutyramide, and 1,3-dimethyl-3,4,5,6-tetrahydro-2(1H)-pyrimidinone.

In certain embodiments, the solvent is non-cyclic. In other embodiments, the non-cyclic solvent is chosen from N,N-dimethyl-acetamide and isobutyramide.

Non-limiting examples of effective amounts of cyclic and/or non-cyclic solvents include, e.g., about 1% to about 95% (v/v). In some embodiments, the concentration of solvent is 5% to 60% (v/v). In other embodiments, the concentration of solvent is 10% to 60% (v/v). In still other embodiments, the concentration of solvent is 30% to 50% (v/v). Concentrations of 1% to 5%, 5% to 10%, 10%, 10% to 20%, 20% to 30%, 30% to 40%, 40% to 50%, or 50% to 60% (v/v) are also suitable. In some embodiments, the solvent will be present at a concentration of 0.1%, 0.25%, 0.5%, 1%, 2%, 3%, 4%, or 5% (v/v). In other embodiments, the solvent will be present at a concentration of 7%, 7.5%, 8%, 8.5%, 9%, 9.5%, 10%, 10.5%, 11%, 11.5%, 12%, 12.5%, 13%, 13.5%, 14%, 14.5%, 15%, 15.5%, 16%, 16.5%, 17%, 17.5%, 18%, 18.5%, 19%, 19.5%, or 20% (v/v).

According to yet another aspect, the invention relates to the use of a composition comprising a hybridization composition as described in this invention for use in hybridization assays.

DETAILED DESCRIPTION

A. Definitions

Figure 1:
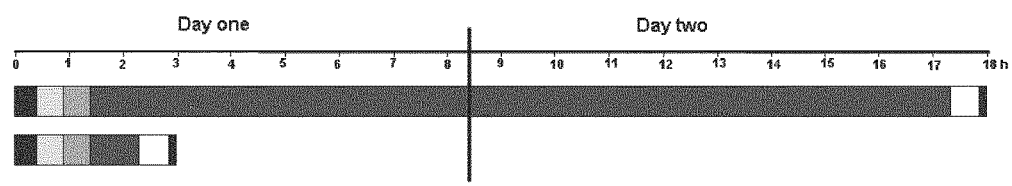
FIG. 1 depicts a typical time-course for single locus detection with primary labeled FISH probes on formaldehyde fixed paraffin embedded tissue sections (histological specimens). The bars represent a hybridization assay performed using a traditional solution (top) and a typical time-course for a hybridization assay performed using a composition of the invention (bottom). The first bar on the left in each time-course represents the deparaffination step; the second bar represents the heat-pretreatment step; the third bar represents the digestion step; the fourth bar represents the denaturation and hybridization steps; the fifth bar represents the stringency wash step; and the sixth bar represents the mounting step.

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular.

In this application, the use of "or" means "and/or" unless stated otherwise. In the context of a multiple dependent claim, the use of "or" refers back to more than one preceding independent or dependent claim in the alternative only.

Unless the meaning is clearly to the contrary, all ranges set forth herein are deemed to be inclusive of the endpoints. In the context of the present invention the following terms are to be understood as follows:

"Biological sample" is to be understood as any in vivo, in vitro, or in situ sample of one or more cells or cell fragments. This can, for example, be a unicellular or multicellular organism, tissue section, cytological sample, chromosome spread, purified nucleic acid sequences, artificially made nucleic acid sequences made by, e.g., a biologic based system or by chemical synthesis, microarray, or other form of nucleic acid chip. In one embodiment, a sample is a mammalian sample, such as, e.g., a human, murine, rat, feline, or canine sample.

"Nucleic acid," "nucleic acid chain," and "nucleic acid sequence" mean anything that binds or hybridizes using base pairing including, oligomers or polymers having a backbone formed from naturally occurring nucleotides and/or nucleic acid analogs comprising nonstandard nucleobases and/or nonstandard backbones (e.g., PNA or LNA), or any derivatized form of a nucleic acid.

As used herein, the term "peptide nucleic acid" or "PNA" means a synthetic polymer having a polyamide backbone with pendant nucleobases (naturally occurring and modified), including, but not limited to, any of the oligomer or polymer segments referred to or claimed as peptide nucleic acids in, e.g., U.S. Pat. Nos. 5,539,082, 5,527,675, 5,623, 049, 5,714,331, 5,718,262, 5,736,336, 5,773,571, 5,766,855, 5,786,461, 5,837,459, 5,891,625, 5,972,610, 5,986,053, 6,107,470 6,201,103, 6,228,982 and 6,357,163, WO96/04000, all of which are herein incorporated by reference, or any of the references cited therein. The pendant nucleobase, such as, e.g., a purine or pyrimidine base on PNA may be connected to the backbone via a linker such as, e.g., one of the linkers taught in PCT/US02/30573 or any of the references cited therein. In one embodiment, the PNA has an N-(2-aminoethyl)-glycine) backbone. PNAs may be synthesized (and optionally labeled) as taught in PCT/US02/30573 or any of the references cited therein. PNAs hybridize tightly, and with high sequence specificity, with DNA and RNA, because the PNA backbone is uncharged. Thus, short PNA probes may exhibit comparable specificity to longer DNA or RNA probes. PNA probes may also show greater specificity in binding to complementary DNA or RNA.

As used herein, the term "locked nucleic acid" or "LNA" means an oligomer or polymer comprising at least one or more LNA subunits. As used herein, the term "LNA subunit" means a ribonucleotide containing a methylene bridge that connects the 2'-oxygen of the ribose with the 4'-carbon. See generally, Kurreck, Eur. J. Biochem., 270:1628-44 (2003).

Examples of nucleic acids and nucleic acid analogs also include polymers of nucleotide monomers, including double and single stranded deoxyribonucleotides (DNA), ribonucleotides (RNA), α-anomeric forms thereof, synthetic and natural analogs thereof, and the like. The nucleic acid chain may be composed entirely of deoxyribonucleotides, ribonucleotides, peptide nucleic acids (PNA), locked nucleic acids (LNA), synthetic or natural analogs thereof, or mixtures thereof. DNA, RNA, or other nucleic acids as defined herein can be used in the method and compositions of the invention.

"Aqueous solution" is to be understood as a solution containing water, even small amounts of water. For example, a solution containing 1% water is to be understood as an aqueous solution.

"Hybridization application," "hybridization assay," "hybridization experiment," "hybridization procedure," "hybridization technique," "hybridization method," etc. are to be understood as referring to any process that involves hybridization of nucleic acids. Unless otherwise specified, the terms "hybridization" and "hybridization step" are to be understood as referring to the re-annealing step of the hybridization procedure as well as the denaturation step.

"Hybridization composition" refers to an aqueous solution of the invention for performing a hybridization procedure, for example, to bind a probe to a nucleic acid sequence. Hybridization compositions may comprise, e.g., a solvent and at least one nucleic acid sequence. Hybridization compositions do not comprise enzymes or other components, such as deoxynucleoside triphosphates (dNTPs), for amplifying nucleic acids in a biological sample.

"Hybridization solution" refers to an aqueous solution for use in a hybridization composition of the invention. Hybridization solutions are discussed in detail below and may comprise, e.g., buffering agents, accelerating agents, chelating agents, salts, detergents, and blocking agents.

"Repetitive Sequences" is to be understood as referring to the rapidly reannealing (approximately 25%) and/or intermediately reannealing (approximately 30%) components of mammalian genomes. The rapidly reannealing components contain small (a few nucleotides long) highly repetitive sequences usually found in tandem (e.g., satellite DNA), while the intermediately reannealing components contain interspersed repetitive DNA. Interspersed repeated sequences are classified as either SINEs (short interspersed repeat sequences) or LINEs (long interspersed repeated sequences), both of which are classified as retrotransposons in primates. SINEs and LINEs include, but are not limited to, Alu-repeats, Kpn-repeats, di-nucleotide repeats, tri-nucleotide repeats, tetra-nucleotide repeats, penta-nucleotide repeats and hexa-nucleotide repeats. Alu repeats make up the majority of human SINEs and are characterized by a consensus sequence of approximately 280 to 300 bp that consist of two similar sequences arranged as a head to tail dimer. In addition to SINEs and LINEs, repeat sequences also exist in chromosome telomeres at the termini of chromosomes and chromosome centromeres, which contain distinct repeat sequences that exist only in the central region of a chromosome. However, unlike SINEs and LINEs, which are dispersed randomly throughout the entire genome, telomere and centromere repeat sequences are localized within a certain region of the chromosome.

"Non-toxic" and "reduced toxicity" are defined with respect to the toxicity labeling of formamide according to "Directive 1999/45/EC of the European Parliament and of the Council of 31 May 1999 concerning the approximation of the laws, regulations and administrative provisions of the Member States relating to the classification, packaging, and labelling of dangerous preparations" (ecb.jrc.it/legislation/1999L0045EC.pdf) ("Directive"). According to the Directive, toxicity is defined using the following classification order: T+"very toxic"; T "toxic", C "corrosive", Xn "harmful", .Xi "irritant." Risk Phrases ("R phrases") describe the risks of the classified toxicity. Formamide is listed as T (toxic) and R61 (may cause harm to the unborn child).

As used herein, the terms "reduced temperature denaturation" and "low temperature denaturation" refer to denaturations performed below about 95° C.

As used herein, the terms "room temperature" and "RT" refer to about 20° C. to about 25° C., unless otherwise stated.

B. Compositions, Buffers, and Solutions (1) Hybridization Solutions

Traditional hybridization solutions are known in the art. Such solutions may comprise, for example, buffering agents, accelerating agents, chelating agents, salts, detergents, and blocking agents.

For example, the buffering agents may include sodium chloride/sodium citrate (SSC), (4-(2-hydroxyethyl)-1-piperazineethanesulfonic acid (HEPES), sodium chloride/sodium phosphate (monobasic)/ethylenediaminetetraacetic acid (SSPE), piperazine-N,N'-bis(2-ethanesulfonic acid) (PIPES), trimellitic anhydride acid chloride (TMAC), Tris (hydroxymethyl)aminomethane (TRIS), sodium dodecyl sulfate/Tris(hydroxymethyl)aminomethane/ethylenediaminetetraacetic (STE), citric acid, a phosphate buffer, such as, e.g., potassium phosphate or sodium pyrrophosphate, etc. In some embodiments, the term "phosphate buffer" refers to a phosphate buffered solution containing $NaH_2PO_4$, $2H_2O$ (sodium phosphate dibasic dihydrate) and $Na_2HPO_4$, $H_2O$ (sodium phosphate monobasic monohydrate). The buffering agents may be present at concentrations from 0.01× to 50×, such as, for example, 0.01×, 0.1×, 0.5×, 1×, 2×, 5×, 10×, 15×, 20×, 25×, 30×, 35×, 40×, 45×, or 50×. Typically, the buffering agents are present at concentrations from 0.1× to 10×.

The accelerating agents may include polymers such as Ficoll, Polyvinylpyrrolidone (PVP), heparin, dextran sulfate, proteins such as Bovine serum albumin (BSA), glycols such as ethylene glycol, glycerol, 1,3 propanediol, propylene glycol, or diethylene glycol, combinations thereof such as Dernhardt's solution and Bovine Lacto Transfer Technique Optimizer (BLOTTO), and organic solvents such as dimethylformamide, Dimethyl sulfoxide (DMSO), etc. The accelerating agent may be present at concentrations from 1% to 80% or 0.1× to 10×, such as, for example, 0.1% (or 0.1×), 0.2% (or 0.2×), 0.5% (or 0.5×), 1% (or 1×), 2% (or 2×), 5% (or 5×), 10% (or 10×), 15% (or 15×), 20% (or 20×), 25% (or 25×), 30% (or 30×), 40% (or 40×), 50% (or 50×), 60% (or 60×), 70% (or 70×), or 80% (or 80×). Typically, DMSO, dextran sulfate, and glycol are present at concentrations from 5% to 10%, such as 5%, 6%, 7%, 8%, 9%, or 10%.

The chelating agents may include Ethylenediaminetetraacetic acid (EDTA), ethylene glycol tetraacetic acid (EGTA), etc. The chelating agents may be present at concentrations from 0.1 mM to 10 mM, such as 0.1 mM, 0.2 mM, 0.5 mM, 1 mM, 2 mM, 3 mM, 4 mM, 5 mM, 6 mM, 7 mM, 8 mM, 9 mM, or 10 mM. Typically, the chelating agents are present at concentrations from 0.5 mM to 5 mM, such as 0.5 mM, 1 mM, 1.5 mM, 2 mM, 2.5 mM, 3 mM, 3.5 mM, 4 mM, 4.5 mM, or 5 mM.

The salts may include sodium chloride (NaCl), sodium phosphate, magnesium phosphate, etc. The salts may be present at concentrations from 1 mM to 750 mM, such as 1 mM, 5 mM, 10 mM, 20 mM, 30 mM, 40 mM, 50 mM, 100 mM, 200 mM, 300 mM, 400 mM, 500 mM, 600 mM, 700 mM, or 750 mM. In some embodiments, the salts are present at concentrations from 1 mM to 1000 mM. In other embodiments, the salts are present at concentrations from 300 mM to 700 mM, 400 mM to 700 mM, or 500 mM to 700 mM.

The detergents may include TWEEN, sodium dodecyl sulfate (SDS), Triton™, CHAPS, deoxycholic acid, etc. The detergent may be present at concentrations from 0.001% to 10%, such as, for example, 0.0001, 0.01, 0.1, 0.5, 1, 2, 3, 4, 5, 6, 7, 8, 9, or 10%. Typically, the detergents are present at concentrations from 0.01% to 1%, such as 0.01%, 0.02%, 0.03%, 0.05%, 0.1%, 0.2%, 0.3%, 0.4%, 0.5%, 0.6%, 0.7%, 0.8%, 0.9%, or 1%.

The nucleic acid blocking agents may include, yeast tRNA, homopolymer DNA, denatured salmon sperm DNA, herring sperm DNA, total human DNA, COT1 DNA, etc. The blocking nucleic acids may be present at concentrations of 0.05 mg/mL to 100 mg/mL.

A great variation exists in the literature regarding traditional hybridization solutions. For example, a traditional hybridization solution may comprise 5× or 6×SSC, 0.01 M EDTA, 5× Dernhardt's solution, 0.5% SDS, and 100 mg/mL sheared, denatured salmon sperm DNA. Another traditional hybridization solution may comprise 50 mM HEPES, 0.5 M NaCl, and 0.2 mM EDTA. A typical hybridization solution for FISH on biological specimens for RNA detection may comprise, e.g., 2×SSC, 10% dextran sulfate, 2 mM vanadyl-ribonucleoside complex, 50% formamide, 0.02% RNAse-free BSA, and 1 mg/mL E. coli tRNA. A typical hybridization solution for FISH on biological specimens for DNA detection may comprise, e.g., 2×SSC, 10% dextran sulfate, 50% formamide, and e.g., 0.3 mg/mL salmon sperm DNA or 0.1 mg/mL COT1 DNA. Other typical hybridization solutions may comprise 40% formamide, 10% dextran sulfate, 300 mM NaCl, 5 mM phosphate buffer, Alu-PNA (blocking PNA) or COT-1 DNA, and in some cases 0.1 µg/µL total human DNA (THD).

The compositions of the invention may comprise a hybridization solution comprising any of the components of traditional hybridization solutions recited above. The traditional components may be present at the same concentrations as used in traditional hybridization solutions, or may be present at higher or lower concentrations, or may be omitted completely.

For example, if the compositions of the invention comprise salts such as NaCl and/or phosphate buffer, the salts may be present at concentrations that are about twice as high as traditional concentrations. For example, in some embodiments, the salts may be present at concentrations of 0-1200 mM NaCl and/or 0-200 mM citrate buffer. In some embodiments, the concentrations of salts may be, for example, 300 mM NaCl and/or 5 mM citrate buffer, or 600 mM NaCl and/or 10 mM citrate buffer.

If the compositions of the invention comprise accelerating agents such as dextran sulfate, glycol, or DMSO, the dextran sulfate may be present at concentrations that are about twice as high as traditional concentrations. For example, in some embodiments, the dextran sulfate may be present at concentrations of from 5% to 40%. In some embodiments, the concentration of dextran sulfate may be 10% or 20%. In some embodiments, the glycol may be present at concentrations of from 0.1% to 10%, and the DMSO may be from 0.1% to 10%. In other embodiments, the concentration of ethylene glycol, 1,3 propanediol, or glycerol may be 1% to 10%. In some embodiments, the concentration of DMSO may be 1%. In some embodiments, the aqueous composition does not comprise DMSO.

If the compositions of the invention comprise citric acid, the concentrations may range from 1 mM to 50 mM and the pH may range from 5.0 to 8.0. In some embodiments the concentration of citric acid may be 10 mM and the pH may be 6.2.

The compositions of the invention may comprise agents that reduce non-specific binding to, for example, the cell membrane, such as salmon sperm or small amounts of total human DNA or, for example, they may comprise blocking agents to block binding of, e.g., repeat sequences to the target such as larger amounts of total human DNA or repeat enriched DNA or specific blocking agents such as PNA or LNA fragments and sequences. These agents may be present at concentrations of from 0.01-100 µg/µL or 0.01-100 µM. For example, in some embodiments, these agents will be 0.1 µg/µL total human DNA, or 0.1 µg/µL non-human DNA, such as herring sperm, salmon sperm, or calf thymus DNA, or 5 µM blocking PNA.

One aspect of the invention is a composition or solution for use in hybridization. Compositions for use in the invention include an aqueous composition comprising a nucleic acid sequence and a solvent. In some embodiments, the solvent is chosen from N,N-dimethyl-acetamide, isobutyramide, tetramethylene sulfoxide, and 1,3-dimethyl-3,4,5,6-tetrahydro-2(1H)-pyrimidinone. In other embodiments, the solvent is non-cyclic.

If the compositions of the invention are used in a hybridization assay, they may further comprise one or more nucleic acid probes. The probes may be directly or indirectly labeled with detectable compounds such as enzymes, chromophores, fluorochromes, and haptens. The DNA probes may be present at concentrations of 0.1 to 100 ng/4. For example, in some embodiments, the probes may be present at concentrations of 1 to 10 ng/4. The PNA probes may be present at concentrations of 0.5 to 5000 nM. For example, in some embodiments, the probes may be present at concentrations of 5 to 1000 nM.

In one embodiment, a composition of the invention comprises a mixture of 15% of N,N-dimethyl-acetamide, isobutyramide, tetramethylene sulfoxide, or 1,3-dimethyl-3,4,5,6-tetrahydro-2(1H)-pyrimidinone, 20% dextran sulfate, 600 mM NaCl, 10 mM citric acid buffer pH 6.2. Another exemplary composition comprises a mixture of 15% of N,N-dimethyl-acetamide, isobutyramide, tetramethylene sulfoxide, or 1,3-dimethyl-3,4,5,6-tetrahydro-2(1H)-pyrimidinone, 20% dextran sulfate, 600 mM NaCl, 10 mM citric acid buffer pH 6.2, and 0.1 µg/µL herring sperm DNA, or salmon sperm DNA, or calf thymus DNA, or 0.5% formamide, or 1% ethylene glycol, or 1% 1,3 propanediol.

(2) Optimization for Particular Applications

The compositions of the invention can be varied in order to optimize results for a particular application. For example, the concentration of cyclic and/or non-cyclic solvents, salt, accelerating agent, blocking agent, and/or hydrogen ions (i.e. pH) may be varied in order to improve results for a particular application. The cyclic and/or non-cyclic solvents is chosen from butadiene sulfone, tetrahydrothiophene 1-oxide (tetramethylene sulfoxide), d-valerolactam (2-piperidone), 2-pyrrolidone, cyclopentanone, N-methyl-2-pyrrolidone, 1,3-dimethyl-3,4,5,6-tetrahydro-2(1H)-pyrimidinone, N,N-dimethyl-acetamide and isobutyramide.

The concentrations of salt and dextran sulfate may also be varied in order to improve signal intensity and background staining Generally, as the concentrations of salt and dextran sulfate increase, the signal intensity may increase while background decreases. Likewise, signal intensity may increase as dextran sulfate concentration increases from, for example, 0% to 20%.

In addition, the types probes used in the compositions of the invention may be varied to improve results. For example, in some aspects of the invention, combinations of DNA/DNA probes may show less background than combinations of DNA/PNA probes in the compositions of the invention or vice versa. On the other hand, PNA probes may tend to show stronger signals than DNA probes, for example, under low salt concentrations.

C. Applications, Methods, and Uses (1) Analytical Samples

The methods and compositions of the invention may be used fully or partly in all types of hybridization applications in the fields of cytology, histology, or molecular biology. According to one embodiment, the first or the second nucleic acid sequence in the methods of the invention is present in a biological sample. Examples of such samples include, e.g., tissue samples, cell preparations, cell fragment preparations, and isolated or enriched cell component preparations. The sample may originate from various tissues such as, e.g., breast (e.g., mammacarcinoma samples), lung, colorectal, prostate, lung, head & neck, stomach, pancreas, esophagus, liver, and bladder, or other relevant tissues and neoplasia thereof, any cell suspension, blood sample, fine needle aspiration, ascites fluid, sputum, peritoneum wash, lung wash, urine, feces, cell scrape, cell smear, cytospin or cytoprep cells.

The sample may be isolated and processed using standard protocols. Cell fragment preparations may, e.g., be obtained by cell homogenizing, freeze-thaw treatment or cell lysing. The isolated sample may be treated in many different ways depending of the purpose of obtaining the sample and depending on the routine at the site. Often the sample is treated with various reagents to preserve the tissue for later sample analysis, alternatively the sample may be analyzed directly. Examples of widely used methods for preserving samples are formalin-fixed followed by paraffin-embedding and cryo-preservation.

For metaphase spreads, cell cultures are generally treated with colcemid, or anther suitable spindle pole disrupting agent, to stop the cell cycle in metaphase. The cells are then fixed and spotted onto microscope slides, treated with formaldehyde, washed, and dehydrated in ethanol. Probes are then added and the samples are analyzed by any of the techniques discussed below.

Cytology involves the examination of individual cells and/or chromosome spreads from a biological sample. Cytological examination of a sample begins with obtaining a specimen of cells, which can typically be done by scraping, swabbing or brushing an area, as in the case of cervical specimens, or by collecting body fluids, such as those obtained from the chest cavity, bladder, or spinal column, or by fine needle aspiration or fine needle biopsy, as in the case of internal tumors. In a conventional manual cytological preparation, the sample is transferred to a liquid suspending material and the cells in the fluid are then transferred directly or by centrifugation-based processing steps onto a glass microscope slide for viewing. In a typical automated cytological preparation, a filter assembly is placed in the liquid suspension and the filter assembly both disperses the cells and captures the cells on the filter. The filter is then removed and placed in contact with a microscope slide. The cells are then fixed on the microscope slide before analysis by any of the techniques discussed below.

In a traditional DNA hybridization experiment using a cytological sample, slides containing the specimen are immersed in a formaldehyde buffer, washed, and then dehydrated in ethanol. The probes are then added and the specimen is covered with a coverslip. The slide is optionally incubated at a temperature sufficient to denature any double-stranded nucleic acid in the specimen (e.g., 5 minutes at 67° C.) and then incubated at a temperature sufficient to allow hybridization (e.g., overnight at 45° C.). After hybridization, the coverslips are removed and the specimens are subjected to a high-stringency wash (e.g., 10 minutes at 65° C.) followed by a series of low-stringency washes (e.g., 2×3 minutes at room temperature). The samples are then dehydrated and mounted for analysis.

In a traditional RNA hybridization experiment using cytological samples, cells are equilibrated in 40% formamide, 1×SSC, and 10 mM sodium phosphate for 5 min, incubated at 37° C. overnight in hybridization reactions containing 20 ng of oligonucleotide probe (e.g., a mix of labeled 50 bp oligos), 1×SSC, 40% formamide, 10% dextran sulfate, 0.4% BSA, 20 mM ribonucleotide vanadyl complex, salmon testes DNA (10 mg/ml), E. coli tRNA (10 mg/ml), and 10 mM sodium phosphate. Then washed twice with 4×SSC/40% formamide and again twice with 2×SSC/40% formamide, both at 37° C., and then with 2×SSC three times at room temperature. Digoxigenin-labeled probes can then e.g. be detected by using a monoclonal antibody to digoxigenin conjugated to Cy3. Biotin-labeled probes can then e.g. be detected by using streptavidin-Cy5. Detection can be by fluorescence or chromogenic, e.g. CISH.

Histology involves the examination of cells in thin slices of tissue. To prepare a tissue sample for histological examination, pieces of the tissue are fixed in a suitable fixative, typically an aldehyde such as formaldehyde or glutaraldehyde, and then embedded in melted paraffin wax. The wax block containing the tissue sample is then cut on a microtome to yield thin slices of paraffin containing the tissue, typically from 2 to 10 microns thick. The specimen slice is then applied to a microscope slide, air dried, and heated to cause the specimen to adhere to the glass slide. Residual paraffin is then dissolved with a suitable solvent, typically xylene, toluene, or others. These so-called deparaffinizing solvents are then removed with a washing-dehydrating type reagent prior to analysis of the sample by any of the techniques discussed below. Alternatively, slices may be prepared from frozen specimens, fixed briefly in 10% formalin or other suitable fixative, and then infused with dehydrating reagent prior to analysis of the sample.

In a traditional DNA hybridization experiment using a histological sample, formalin-fixed paraffin embedded tissue specimens are cut into sections of 2-6 µm and collected on slides. The paraffin is melted (e.g., 30-60 minutes at 60° C.) and then removed (deparaffinated) by washing with xylene (or a xylene substitute), e.g., 2×5 minutes. The samples are rehydrated, washed, and then pre-treated (e.g., 10 minutes at 95-100° C.). The slides are washed and then treated with pepsin or another suitable permeabilizer, e.g., 3-15 minutes at 37° C. The slides are washed (e.g., 2×3 minutes), dehydrated, and probe is applied. The specimens are covered with a coverslip and the slide is optionally incubated at a temperature sufficient to denature any double-stranded nucleic acid in the specimen (e.g., 5 minutes at 67° C.), followed by incubation at a temperature sufficient to allow hybridization (e.g., overnight at 45° C.). After hybridization, the coverslips are removed and the specimens are subjected to a high-stringency wash (e.g., 10 minutes at 65° C.) followed by a series of low-stringency washes (e.g., 2×3 minutes at room temperature). The samples are then dehydrated and mounted for analysis.

In a traditional RNA hybridization experiment using a histological sample, slides with FFPE tissue sections are deparaffinized in xylene for 2×5 min, immersed in 99% ethanol 2×3 min, in 96% ethanol 2×3 min, and then in pure water for 3 min. Slides are placed in a humidity chamber, Proteinase K is added, and slides are incubated at RT for 5-15 min. Slides are immersed in pure water for 2×3 min, immersed in 96% ethanol for 10 sec, and air-dried for 5 min. Probes are added to the tissue section and covered with coverslip. The slides are incubated at 55° C. in humidity chamber for 90 min. After incubation, the slides are immersed in a stringent wash solution at 55° C. for 25 min, and then immersed in TBS for 10 sec. The slides are incubated in a humidity chamber with antibody for 30 min. The slides are immersed in TBS for 2×3 min, then in pure water for 2×1 min, and then placed in a humidity chamber. The slides are then incubated with substrate for 60 min, and immersed in tap water for 5 min.

In a traditional northern blot procedure, the RNA target sample is denatured for 10 minutes at 65° C. in RNA loading buffer and immediately placed on ice. The gels are loaded and electrophoresed with 1×MOPS buffer (10×MOPS contains 200 mM morpholinopropansulfonic acid, 50 mM sodium acetate, 10 mM EDTA, pH 7.0) at 25 V overnight. The gel is then pre-equilibrated in 20×SSC for 10 min and the RNA is transferred to a nylon membrane using sterile 20×SSC as transfer buffer. The nucleic acids are then fixed on the membrane using, for example, UV-cross linking at 120 mJ or baking for 30 min at 120° C. The membrane is then washed in water and air dried. The membrane is placed in a sealable plastic bag and prehybridized without probe for 30 min at 68° C. The probe is denatured for 5 min at 100° C. and immediately placed on ice. Hybridization buffer (prewarmed to 68° C.) is added and the probe is hybridized at 68° C. overnight. The membrane is then removed from the bag and washed twice for 5 min each with shaking in a low stringency wash buffer (e.g., 2×SSC, 0.1% SDS) at room temperature. The membrane is then washed twice for 15 min each in prewarmed high stringency wash buffer (e.g., 0.1× SSC, 0.1% SDS) at 68° C. The membrane may then be stored or immediately developed for detection.

Additional examples of traditional hybridization techniques can be found, for example, in Sambrook et al., *Molecular Cloning A Laboratory Manual*, 2$^{nd}$ Ed., Cold Spring Harbor Laboratory Press, (1989) at sections 1.90-1.104, 2.108-2.117, 4.40-4.41, 7.37-7.57, 8.46-10.38, 11.7-11.8, 11.12-11.19, 11.38, and 11.45-11.57; and in Ausubel et al., *Current Protocols in Molecular Biology*, John Wiley & Sons, Inc. (1998) at sections 2.9.1-2.9.6, 2.10.4-2.10.5, 2.10.11-2.10.16, 4.6.5-4.6.9, 4.7.2-4.7.3, 4.9.7-4.9.15, 5.9.18, 6.2-6.5, 6.3, 6.4, 6.3.3-6.4.9, 5.9.12-5.9.13, 7.0.9, 8.1.3, 14.3.1-14.3.4, 14.9, 15.0.3-15.0.4, 15.1.1-15.1.8, and 20.1.24-20.1.25.

(2) Hybridization Techniques

The compositions and methods of the present invention can be used fully or partly in all types of nucleic acid hybridization techniques known in the art for cytological and histological samples. Such techniques include, for example, in situ hybridization (ISH), fluorescent in situ hybridization (FISH; including multi-color FISH, Fiber-FISH, etc.), chromogenic in situ hybridization (CISH), silver in situ hybridization (SISH), comparative genome hybridization (CGH), chromosome paints, and arrays in situ.

Molecular probes that are suitable for use in the hybridizations of the invention are described, e.g., in U.S. Patent Publication No. 2005/0266459, which is incorporated herein by reference. In general, probes may be prepared by chemical synthesis, PCR, or by amplifying a specific DNA sequence by cloning, inserting the DNA into a vector, and amplifying the vector an insert in appropriate host cells. Commonly used vectors include bacterial plasmids, cosmids, bacterial artificial chromosomes (BACs), PI diverted artificial chromosomes (PACs), or yeast artificial chromosomes (YACs). The amplified DNA is then extracted and purified for use as a probe. Methods for preparing and/or synthesizing probes are known in the art, e.g., as disclosed in PCT/US02/30573.

In general, the type of probe determines the type of feature one may detect in a hybridization assay. For example, total nuclear or genomic DNA probes can be used as a species-specific probe. Chromosome paints are collections of DNA sequences derived from a single chromosome type and can identify that specific chromosome type in metaphase and interphase nuclei, count the number of a certain chromosome, show translocations, or identify extra-chromosomal fragments of chromatin. Different chromosomal types also have unique repeated sequences that may be targeted for probe hybridization, to detect and count specific chromosomes. Large insert probes may be used to target unique single-copy sequences. With these large probes, the hybridization efficiency is inversely proportional to the probe size. Smaller probes can also be used to detect aberrations such as deletions, amplifications, inversions, duplications, and aneuploidy. For example, differently-colored locus-specific probes can be used to detect translocations via split-signal in situ hybridization.

In general, the ability to discriminate between closely related sequences is inversely proportional to the length of the hybridization probe because the difference in thermal stability decreases between wild type and mutant complexes as probe length increases. Probes of greater than 10 bp in length are generally required to obtain the sequence diversity necessary to correctly identify a unique organism or clinical condition of interest. On the other hand, sequence differences as subtle as a single base (point mutation) in very short oligomers (<10 base pairs) can be sufficient to enable the discrimination of hybridization to complementary nucleic acid target sequences as compared with non-target sequences.

In one embodiment, at least one set of the in situ hybridization probes may comprise one or more PNA probes, as defined above and as described in U.S. Pat. No. 7,105,294, which is incorporated herein by reference. Methods for synthesizing PNA probes are described in PCT/US02/30573. Alternatively, or in addition, at least one set of the hybridization probes in any of the techniques discussed above may comprise one or more locked nucleic acid (LNA) probes, as described in WO 99/14226, which is incorporated herein by reference. Due to the additional bridging bond between the 2' and 4' carbons, the LNA backbone is pre-organized for hybridization. LNA/DNA and LNA/RNA interactions are stronger than the corresponding DNA/DNA and DNA/RNA interactions, as indicated by a higher melting temperature. Thus, the compositions and methods of the invention, which decrease the energy required for hybridization, are particularly useful for hybridizations with LNA probes.

In one embodiment, the probes may comprise a detectable label (a molecule that provides an analytically identifiable signal that allows the detection of the probe-target hybrid), as described in U.S. Patent Publication No. 2005/0266459, which is incorporated herein by reference. The probes may be labeled to make identification of the probe-target hybrid possible by use, for example, of a fluorescence or bright field microscope/scanner. In some embodiments, the probe may be labeled using radioactive labels such as $^{31}P$, $^{33}P$, or $^{32}S$, non-radioactive labels such as digoxigenin and biotin, or fluorescent labels. The detectable label may be directly attached to a probe, or indirectly attached to a probe, e.g., by using a linker. Any labeling method known to those in the art, including enzymatic and chemical processes, can be used for labeling probes used in the methods and compositions of the invention. In other embodiments, the probes are not labeled.

In general, in situ hybridization techniques such as CGH, FISH, CISH, and SISH, employ large, mainly unspecified, nucleic acid probes that hybridize with varying stringency to genes or gene fragments in the chromosomes of cells. Using large probes renders the in situ hybridization technique very sensitive. However, the successful use of large genomic probes in traditional hybridization assays depends on blocking the undesired background staining derived from, e.g., repetitive sequences that are present throughout the genome. Traditional methods for decreasing nonspecific probe binding include saturating the binding sites on proteins and tissue by incubating tissue with prehybridization solutions containing ficoll, bovine serum albumin (BSA), polyvinyl pyrrolidone, and nucleic acids. Such blocking steps are time-consuming and expensive. Advantageously, the methods and compositions of the invention reduce and/or eliminate the need for such blocking steps. However, in one embodiment, repetitive sequences may be suppressed according to the methods known in the art, e.g., as disclosed in PCT/US02/30573.

Bound probes may be detected in cytological and histological samples either directly or indirectly with fluorochromes (e.g., FISH), organic chromogens (e.g., CISH), silver particles (e.g., SISH), or other metallic particles (e.g., gold-facilitated fluorescence in situ hybridization, GOLD-FISH). Thus, depending on the method of detection, populations of cells obtained from a sample to be tested may be visualized via fluorescence microscopy or conventional brightfield light microscopy.

Hybridization assays on cytological and histological samples are important tools for determining the number, size, and/or location of specific DNA sequences. For example, in CGH, whole genomes are stained and compared to normal reference genomes for the detection of regions with aberrant copy number. Typically, DNA from subject tissue and from normal control tissue is labeled with different colored probes. The pools of DNA are mixed and added to a metaphase spread of normal chromosomes (or to a microarray chip, for array- or matrix-CGH). The ratios of colors are then compared to identify regions with aberrant copy number.

FISH is typically used when multiple color imaging is required and/or when the protocol calls for quantification of signals. The technique generally entails preparing a cytological sample, labeling probes, denaturing target chromosomes and the probe, hybridizing the probe to the target sequence, and detecting the signal. Typically, the hybridization reaction fluorescently stains the targeted sequences so that their location, size, or number can be determined using fluorescence microscopy, flow cytometry, or other suitable instrumentation. DNA sequences ranging from whole genomes down to several kilobases can be studied using FISH. With enhanced fluorescence microscope techniques, such as, for example, deconvolution, even a single mRNA molecule can be detected. FISH may also be used on metaphase spreads and interphase nuclei.

FISH has been used successfully for mapping repetitive and single-copy DNA sequences on metaphase chromosomes, interphase nuclei, chromatin fibers, and naked DNA molecules, and for chromosome identification and karyotype analysis through the localization of large repeated families, typically the ribosomal DNAs and major tandem array families. One of the most important applications for FISH has been in detecting single-copy DNA sequences, in particular disease related genes in humans and other eukaryotic model species, and the detection of infectious agents. FISH may be used to detect, e.g., chromosomal aneuploidy in prenatal diagnoses, hematological cancers, and solid tumors; gene abnormalities such as oncogene amplifications, gene deletions, or gene fusions; chromosomal structural abnormalities such as translocations, duplications, insertions, or inversions; contiguous gene syndromes such as microdeletion syndrome; the genetic effects of various therapies; viral nucleic acids in somatic cells and viral integration sites in chromosomes; etc. In multi-color FISH, each chromosome is stained with a separate color, enabling one to determine the normal chromosomes from which abnormal chromosomes are derived. Such techniques include multiplex FISH (m-FISH), spectral karyotyping (SKY), combined binary ration labeling (COBRA), color-changing karyotyping, cross-species color banding, high resolution multicolor banding, telomeric multiplex FISH (TM-FISH), split-signal FISH (ssFISH), and fusion-signal FISH.

CISH and SISH may be used for many of the same applications as FISH, and have the additional advantage of allowing for analysis of the underlying tissue morphology, for example, in histopathology applications. If FISH is performed, the hybridization mixture may contain sets of distinct and balanced pairs of probes, as described in U.S. Pat. No. 6,730,474, which is incorporated herein by reference. For CISH, the hybridization mixture may contain at least one set of probes configured for detection with one or more conventional organic chromogens, and for SISH, the hybridization mixture may contain at least one set of probes configured for detection with silver particles, as described in Powell R D et al., "Metallographic in situ hybridization," Hum. Pathol., 38:1145-59 (2007).

The compositions of the invention may also be used fully or partly in all types of molecular biology techniques involving hybridization, including blotting and probing (e.g., Southern, northern, etc.), and arrays. In some embodiments, the methods and compositions of the invention are useful for nucleic acid hybridization applications, with the proviso that such applications do not include amplification of the nucleic acid such as, e.g., by PCR, in situ PCR, etc.

(3) Hybridization Conditions

The method of the present invention involves the use of compositions comprising at least one nucleic acid sequence and at least one solvent in hybridization of nucleic acid chains. The compositions of the present invention are particularly useful in said method.

Hybridization methods using the compositions of the invention may involve applying the compositions to a sample comprising a target nucleic acid sequence, most likely in a double stranded form. Usually, in order to secure access for the probe to hybridize with the target sequence, the sample and composition are heated to denature the target nucleic acids. During denaturation the solvent interacts with the sequence and facilitates the denaturation of the target and the re-annealing of the probe to target.

Hybridizations using the compositions of the invention may be performed using the same assay methodology as for hybridizations performed with traditional compositions. However, the compositions of the invention allow for shorter hybridization times. For example, the heat pretreatment, digestion, denaturation, hybridization, washing, and mounting steps may use the same conditions in terms of volumes, temperatures, reagents and incubation times as for traditional compositions. Additionally, the compositions of the invention allow for reduction of the hybridization time in methods comprising longer hybridization probes or fragments of hybridization probes, for example, hybridization probes or fragments of hybridization probes comprising 40 to 500 nucleotides, hybridization probes or fragments of hybridization probes comprising 50 to 500 nucleotides, or hybridization probes or fragments of hybridization probes comprising 50 to 200 nucleotides. A great variation exists in the traditional hybridization protocols known in the art. For example, some protocols specify a separate denaturation step of potential double stranded nucleotides without probe present, before the following hybridization step, whereas other protocols will denature the probe and sample together. The compositions of the invention may be used in any of the traditional hybridization protocols known in the art.

Alternatively, assays using the compositions of the invention can be changed and optimized from traditional methodologies, for example, by decreasing the hybridization time, decreasing the hybridization temperatures, and/or decreasing the hybridization volumes.

For example, in some embodiments, the denaturation temperature is 60 to 70° C., 70 to 80° C., 80 to 85° C., 80 to 90° C., or 90 to 100° C. In other embodiments, the denaturation temperature is 70 to 90° C., 72 to 92° C., or 75 to 95° C. In other embodiments, the denaturation temperature is 67° C.

In some embodiments, the compositions of the invention will produce strong signals when the denaturation temperature is from 60 to 100° C. and the hybridization temperature is from 20 to 60° C. In other embodiments, the compositions of the invention will produce strong signals when the denaturation temperature is from 60 to 70° C., 70 to 80° C., 80 to 85° C., 80 to 90° C., or 90 to 100° C., and the hybridization temperature is from 20 to 30° C., 30 to 40° C., 40 to 50° C., or 50 to 60° C. In other embodiments, the compositions of the invention will produce strong signals when the denaturation temperature is 65, 67, 70, or 72° C., and the hybridization temperature is 21, 37, 40, 45, or 50° C. In some embodiments, the compositions of the invention will produce strong signals when the denaturation temperature is 67° C. and the hybridization temperature is 45° C. In other embodiments, the compositions of the invention will produce strong signals when the denaturation temperature is 85° C. and the hybridization temperature is 45° C.

In other embodiments, the compositions of the invention will produce strong signals when the denaturation time is from 0 to 15 minutes and the hybridization time is from 0 minutes to 24 hours. In other embodiments, the compositions of the invention will produce strong signals when the denaturation time is from 0 to 5 minutes and the hybridization time is from 0 minute to 8 hours. In other embodiments, the compositions of the invention will produce strong signals when the denaturation time is 0, 1, 2, 3, 4, or 5 minutes, and the hybridization time is 0 minutes, 5 minutes, 15 minutes, 30 minutes, 60 minutes, 180 minutes, or 240 minutes. It will be understood by those skilled in the art that in some cases, e.g., RNA detection, a denaturation step is not required with traditional buffers. The compositions of the invention also eliminate the need for a denaturation step and/or reduce the temperature required for denaturation of other types of nucleic acids such as, for example, DNA. Thus, in one embodiment, the hybridization time is 0 minutes, i.e., the denaturation step required with prior art buffers is completely eliminated.

Figure 2:
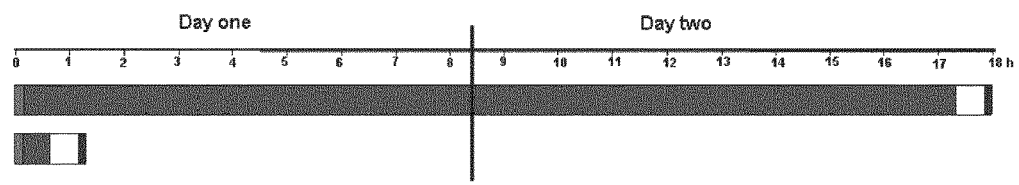
FIG. 2 depicts a typical time-course for single locus detection with primary labeled FISH probes on cytological specimens. The bars represent a hybridization assay performed using a traditional solution (top) and a typical time-course for a hybridization assay performed using a composition of the invention (bottom). The first bar on the left in each time-course represents the fixation step; the second bar represents the denaturation and hybridization steps; the third bar represents the stringency wash step; and the fourth bar represents the mounting step.

Accordingly, hybridizations using the compositions of the invention may be performed in less than 8 hours. In other embodiments, the hybridization step is performed in less than 6 hours. In still other embodiments, the hybridization step is performed within 4 hours. In other embodiments, the hybridization step is performed within 3 hours. In yet other embodiments, the hybridization step is performed within 2 hours. In other embodiments, the hybridization step is performed within 1 hour. In still other embodiments, the hybridization step is performed within 30 minutes. In other embodiments, the hybridization step can take place within 15 minutes. The hybridization step can even take place within 10 minutes or in less than 5 minutes. FIGS. 1 and 2 illustrate a typical time-course for hybridization applications performed on histological and cytological samples, respectively, using the compositions of the invention compared to hybridization applications using a traditional compositions.

Alternatively, assays using the compositions of the invention can be changed and optimized from traditional methodologies, for example, by decreasing the stringent wash time and/or decreasing the stringent wash temperatures.

After complementary strands of nucleic acid have reannealed in a hybridization application, the hybridization product will generally comprise complementary base pairing and non-complementary base pairing between the probe and the target nucleic acid. Any non-complementary base pairing is then removed by a series of post-hybridization washes. Four variables are typically adjusted to influence the stringency of the post-hybridization washes:

1. Temperature (as temperature increases, non-perfect matches between the probe and the target sequence will denature, i.e., separate, before more perfectly matched sequences).
2. Salt conditions (as salt concentration decreases, non-perfect matches between the probe and the target sequence will denature, i.e., separate, before more perfectly matched sequences).
3. Formamide concentration (as the amount of formamide increases, non-perfect matches between the probe and the target sequence will denature, i.e., separate, before more perfectly matched sequences).
4. Time (as the wash time increases, non-perfect matches between the probe and the target sequence will denature, i.e., separate, before more perfectly matched sequences).

Stringent wash methods using the compositions of the invention may involve applying the compositions to a hybridization product comprising a target nucleic acid sequence hybridized to a probe. During the stringent wash step, the cyclic and/or non-cyclic solvent interacts with the hybridization product and facilitates the denaturation of the mismatched (i.e., non-complementary) sequences. The cyclic and/or non-cyclic solvents specified in the present invention may speed up this process, reduce the temperature required for the stringency wash, and reduce the harshness and toxicity of the stringency wash conditions compared to formamide-containing buffers.

Those skilled in the art will understand that different type of hybridization assays, different types of samples, different types of probe targets, different length of probes, different types of probes, e.g. DNA/RNA/PNA/LNA oligos, short DNA/RNA probes (0.5-3 kb), chromosome paint probes, CGH, repetitive probes (e.g. alpha-satellite repeats), single-locus etc., will effect the concentrations of e.g. salt and cyclic and/or non-cyclic solvents required to obtain the most effective post-hybridization washes. The temperature and incubation time are also important variables for stringent washes using the compositions of the invention. In view of the guidance provided herein, one skilled in the art will understand how to vary these factors to optimize the stringency washes in hybridization applications.

Hybridization methods using the compositions of the invention may also involve applying the compositions to a sample comprising a target nucleic acid sequence, most likely in a double stranded form. Usually, in order to secure access for the probe to hybridize with the target sequence, the probe and sample are heated together to denature any double stranded nucleic acids. It has been argued that separate denaturation preserves morphology better, whereas co-denaturation reduces the number of practical steps. For these reasons, separate denaturation steps are most often used in molecular cytogenetics applications, and co-denaturation is most often used when tissue sections are analyzed.

Denaturation typically is performed by incubating the target and probe (either together or separately) in the presence of heat (e.g., at temperatures from about 70° C. to about 95° C.) and cyclic and/or non-cyclic solvents. For example, chromosomal DNA can be denatured by a combination of temperatures above 70° C. (e.g., about 73° C.) and a denaturation buffer containing 70% cyclic and/or non-cyclic solvent and 2×SSC (0.3M sodium chloride and 0.03M sodium citrate). Denaturation conditions typically are established such that cell morphology is preserved.

Furthermore, the compositions of the invention allow for fast hybridizations using longer probes or fragments of probes, for example, probes or fragments of probes comprising 40-500 nucleotides, probes or fragments of probes comprising 50-500 nucleotides, or probes or fragments of probes comprising 50-200 nucleotides.

As hybridization time changes, the concentration of probe may also be varied in order to produce strong signals and/or reduce background. For example, as hybridization time decreases, the amount of probe may be increased in order to improve signal intensity. On the other hand, as hybridization time decreases, the amount of probe may be decreased in order to improve background staining.

The compositions of the invention also reduce or eliminate the need for a blocking step during hybridization applications by improving signal and background intensity by blocking the binding of, e.g., repetitive sequences to the target DNA. Thus, there is no need to use total human DNA, blocking-PNA, COT-1 DNA, or DNA from any other source as a blocking agent. However, background levels can be further reduced by adding agents that reduce non-specific binding, such as to the cell membrane, such as small amounts of total human DNA or non-human-origin DNA (e.g., salmon sperm DNA) to a hybridization reaction using the compositions of the invention.

The aqueous compositions of the invention furthermore provide for the possibility to considerably reduce the concentration of nucleic acid sequences included in the composition. Generally, the concentration of probes may be reduced from 2 to 8-fold compared to traditional concentrations. For example, if HER2 DNA probes and CEN17 PNA probes are used in the compositions of the invention, their concentrations may be reduced by 2 to 20-fold compared to their concentrations in traditional hybridization compositions. In other embodiments, the probe concentrations are independently reduced by 2-fold, 3-fold, 4-fold, 5-fold, 6-fold 7-fold, 8-fold, 9-fold, or 10-fold. This feature, along with the absence of any requirement for blocking DNA, such as blocking-PNA or COT1, allows for an increased probe volume in automated instrument systems compared to the traditional 10 µL volume used in traditional systems, which reduces loss due to evaporation, as discussed in more detail below.

Reducing probe concentration also reduces background. However, reducing the probe concentration is inversely related to the hybridization time, i.e., the lower the concentration, the higher hybridization time required. Nevertheless, even when extremely low concentrations of probe are used with the aqueous compositions of the invention, the hybridization time is still shorter than with traditional compositions.

The compositions of the invention often allow for better signal-to-noise ratios than traditional hybridization compositions. For example, with certain probes, a one hour hybridization with the compositions of the invention will produce similar background and stronger signals than an overnight hybridization in a traditional compositions. Background is not seen when no probe is added.

Traditional assay methods may also be changed and optimized when using the compositions of the invention depending on whether the system is manual, semi-automated, or automated.

For example, a semi-automated or a fully automated system will benefit from the short hybridization times obtained with the compositions of the invention. These changes to traditional hybridization methods may reduce the difficulties encountered when traditional compositions are used in such systems. For example, one problem with semi-automated and fully automated systems is that significant evaporation of the sample can occur during hybridization, since such systems require small sample volumes (e.g., 10-150 µL), elevated denaturation temperatures, and extended hybridization times (e.g., 14 hours). Thus, proportions of the components in traditional hybridization compositions are fairly invariable. However, since the compositions of the invention allow for faster hybridizations, evaporation is reduced, allowing for increased flexibility in the proportions of the components in hybridization compositions used in semi-automated and fully automated systems.

Thus, the compositions and methods of the invention solve many of the problems associated with traditional hybridization compositions and methods.

The disclosure may be understood more clearly with the aid of the non-limiting examples that follow, which constitute preferred embodiments of the compositions according to the disclosure. Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained herein. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope are approximations, the numerical values set forth in the specific example are reported as precisely as possible. Any numerical value, however, inherently contains certain errors necessarily resulting from the standard deviation found in its respective testing measurements. The examples that follow illustrate the present invention and should not in any way be considered as limiting the invention.

EXAMPLES

Reference will now be made in detail to specific embodiments of the invention. While the invention will be described in conjunction with these embodiments, it will be understood that they are not intended to limit the invention to those embodiments. On the contrary, the invention is intended to cover alternatives, modifications, and equivalents, which may be included within the invention as defined by the appended claims.

The reagents used in the following examples are from Dako's Histology FISH Accessory Kit (K5599) (Dako Denmark A/S, Glostrup Denmark). The kits contain all the key reagents, except for probe, required to complete a FISH procedure for formalin-fixed, paraffin-embedded tissue section specimens. All samples were prepared according to the manufacturer's description. The Dako Hybridizer (S2451, Dako) was used for the digestion, denaturation, and hybridization steps.

Evaluation of FISH slides was performed within a week after hybridization using a Leica DM6000B fluorescence microscope, equipped with DAPI, FITC, Texas Red single filters and FITC/Texas Red double filter under 10×, 20×, 40×, and 100× oil objective.

In the Examples that follow, "dextran sulfate" refers to the sodium salt of dextran sulfate (D8906, Sigma) having a molecular weight $M_w>500,000$. All concentrations of solvents are provided as v/v percentages. Citrate buffer refers to a citrate buffered solution containing sodium citrate ($Na_3C_6H_5O_7$, $2H_2O$; 1.06448, Merck) and citric acid monohydrate ($C_6H_8O_7$, $H_2O$; 1.00244, Merck).

General Histology FISH Procedure for Below Examples 1-4

Slides with cut formalin-fixed paraffin embedded (FFPE) multiple tissue array sections from humans (tonsils, mammacarcinoma, kidney, and colon) were baked at 60° C. for 30-60 min, deparaffinated in xylene baths, rehydrated in ethanol baths, and then transferred to Wash Buffer. The samples were then pre-treated in Pre-Treatment Solution at a minimum of 95° C. for 10 min and washed 2×3 min. The samples were then digested with Pepsin RTU at 37° C. for 3 min, washed 2×3 min, dehydrated in a series of ethanol evaporations, and air-dried. The samples were then incubated with 10 µL FISH probe as described under the individual experiments. The samples were then washed with Stringency Wash buffer at 65° C. 10 min, then washed in Wash Buffer for 2×3 min, then dehydrated in a series of ethanol evaporations, and air-dried. Finally, the slides were mounted with 15 µL Antifade Mounting Medium. When the staining was completed, observers trained to assess signal intensity, morphology, and background of the stained slides performed the scoring.

Scoring Guidelines

The signal intensities were evaluated on a 0-3 scale with 0 meaning no signal and 3 equating to a strong signal. Between 0 and 3 there are additional grades 0.5 apart from which the observer can assess signal intensity and background.

The signal intensity is scored after a graded system on a 0-3 scale.
0 No signal is seen.
1 The signal intensity is weak.
2 The signal intensity is moderate.
3 The signal intensity is strong.
The scoring system allows the use of ½ grades.
The background is scored after a graded system on a 0-3 scale.
0 Little to no background is seen.
1 Some background.
2 Moderate background.
3 High Background.
The scoring system allows the use of ½ grades.

Example 1

This example compares the signal intensity and background from three DNA probes and one PNA probe on FFPE tissue sections using different solvents, at a denaturation temperature of 67° C. for 10 min or at 82° C. for 5 min.

FISH Probe Composition I: 3.3 ng/µL HER2 TxRed labeled DNA probe (⅓ of standard concentration) (size 218 kb) and ½ of the standard concentration (300 nM) of CEN17 FITC labeled PNA probes (both probes identical with probes from HER2 FISH pharmDx™ kit (K5331, Dako)); 15% ethylene carbonate (E26258, Sigma-Aldrich); 20% dextran sulfate; 600 mM NaCl; 10 mM citrate buffer, pH 6.2

FISH Probe Composition II: 3.3 ng/µL HER2 TxRed labeled DNA probe (⅓ of standard concentration) (size 218 kb) and ½ of the standard concentration (300 nM) of CEN17 FITC labeled PNA probes (both probes identical with probes from HER2 FISH pharmDx™ kit (K5331, Dako)); 15% Butadiene Sulfone (B84505 Sigma-Aldrich); 20% dextran sulfate; 600 mM NaCl; 10 mM citrate buffer, pH 6.2

FISH Probe Composition III: 3.3 ng/µL HER2 TxRed labeled DNA probe (⅓ of standard concentration) (size 218 kb) and ½ of the standard concentration (300 nM) of CEN17 FITC labeled PNA probes (both probes identical with probes from HER2 FISH pharmDx™ kit (K5331, Dako)); 15% Tetra-methylene sulfoxide (T22403, Sigma-Aldrich); 20% dextran sulfate; 600 mM NaCl; 10 mM citrate buffer, pH 6.2

FISH Probe Composition IV: 3.3 ng/µL HER2 TxRed labeled DNA probe (⅓ of standard concentration) (size 218 kb) and ½ of the standard concentration (300 nM) of CEN17 FITC labeled PNA probes (both probes identical with probes from HER2 FISH pharmDx™ kit (K5331, Dako)); 15% d-valerolactam (V209, Sigma-Aldrich); 20% dextran sulfate; 600 mM NaCl; 10 mM citrate buffer, pH 6.2

FISH Probe Composition V: 3.3 ng/µL HER2 TxRed labeled DNA probe (⅓ of standard concentration) (size 218 kb) and ½ of the standard concentration (300 nM) of CEN17 FITC labeled PNA probes (both probes identical with probes from HER2 FISH pharmDx™ kit (K5331, Dako)); 15% cyclopentanone (08299, Fluka Analytical/Sigma-Aldrich); 20% dextran sulfate; 600 mM NaCl; 10 mM citrate buffer, pH 6.2.

FISH Probe Composition VI: 3.3 ng/µL HER2 TxRed labeled DNA probe (⅓ of standard concentration) (size 218 kb) and ½ of the standard concentration (300 nM) of CEN17 FITC labeled PNA probes (both probes identical with probes from HER2 FISH pharmDx™ kit (K5331, Dako)); 15% 2-pyrrolidone (240338, Sigma-Aldrich); 20% dextran sulfate; 600 mM NaCl; 10 mM citrate buffer, pH 6.2.

FISH Probe Composition VII: 3.3 ng/µL HER2 TxRed labeled DNA probe (⅓ of standard concentration) (size 218 kb) and ½ of the standard concentration (300 nM) of CEN17 FITC labeled PNA probes (both probes identical with probes from HER2 FISH pharmDx™ kit (K5331, Dako)); 15% N-methyl-2-pyrrolidone (806722500, Merck); 20% dextran sulfate; 600 mM NaCl; 10 mM citrate buffer, pH 6.2.

The FISH probes were incubated on FFPE tissue sections for the indicated temperature, for the indicated amount of time, then at 45° C. for 60 min.

Results:

| Composition | Denaturation Temperature | Denaturation Time | Background | Signal Intensity Tx Red FITC |
|---|---|---|---|---|
| I | 67° C. | 10 min | +1 | 3 DNA 3 PNA |
| II | 67° C. | 10 min | +2-2½ | 1½ DNA 2½ PNA |
| III | 67° C. | 10 min | +0 | 2 DNA 3 PNA |
| IV | 67° C. | 10 min | +0 | 3 DNA 3 PNA |
| V | 67° C. | 10 min | +2½ | 2 DNA 3 PNA |
| VI | 67° C. | 10 min | +½ | 3 DNA 3 PNA |
| VII | 67° C. | 10 min | +0 | 2 DNA 3 PNA |
| I | 82° C. | 5 min | +0-2½ | 3 DNA 3 PNA |
| II | 82° C. | 5 min | +2-2½ | 2½-3 DNA 2½-3 PNA |
| III | 82° C. | 5 min | +½ | 2½ DNA 3 PNA |
| IV | 82° C. | 5 min | +1½ | 3 DNA 3 PNA |
| V | 82° C. | 5 min | +3 | 2 DNA 2½-3 PNA |
| VI | 82° C. | 5 min | +½ | 3 DNA 3 PNA |
| VII | 82° C. | 5 min | +0-½ | 2 DNA 3 PNA |

The scoring was performed on the mamma-carcinoma tissue of a multi-tissue section. All buffers were not, except for ethylene carbonate, present in one phase at room temperature (RT) at the used composition concentrations. Denaturation at 82° C. led to increased background for the DNA probes of e.g. ethylene carbonate (composition I), but not for e.g. composition III, IV and VI.

Example 2

This example compares the signal intensity and background from DNA probes and PNA probes on FFPE tissue sections using different solvents, at a denaturation temperature of 67° C. for 10 min and hybridization at 45° C. for 60 min.

FISH Probe Composition I: 3.3 ng/µL HER2 TxRed labeled DNA probe (⅓ of standard concentration) (size 218 kb) and ½ of the standard concentration (300 nM) of CEN17 FITC labeled PNA probes (both probes identical with probes from HER2 FISH pharmDx™ kit (K5331, Dako)); 15% ethylene carbonate (E26258, Sigma-Aldrich); 20% dextran sulfate; 600 mM NaCl; 10 mM citrate buffer, pH 6.2

FISH Probe Composition II: 3.3 ng/µL HER2 TxRed labeled DNA probe (⅓ of standard concentration) (size 218 kb) and ½ of the standard concentration (300 nM) of CEN17 FITC labeled PNA probes (both probes identical with probes from HER2 FISH pharmDx™ kit (K5331, Dako)); 15% 1,3-dimethyl-3,4,5,6-tetrahydro-2(1H)-pyrimidinone (251569, Sigma-Aldrich); 20% dextran sulfate; 600 mM NaCl; 10 mM citrate buffer, pH 6.2

| Composition | Background | Signal Intensity Tx Red FITC |
|---|---|---|
| I | +2 | 3 DNA 3 PNA |
| II | +½ | 2 DNA 2½-3 PNA |

The scoring was performed on the mamma-carcinoma tissue of a multi-tissue section. Composition II was two-phased at the used composition concentrations.

Example 3

This example compares the signal intensity and background from DNA probes and PNA probes on FFPE tissue sections using two non-cyclic solvents, at a denaturation temperature of 67° C. for 10 min and hybridization at 45° C. for 60 min.

FISH Probe Composition I: 3.3 ng/µL HER2 TxRed labeled DNA probe (⅓ of standard concentration) (size 218 kb) and ½ of the standard concentration (300 nM) of CEN17 FITC labeled PNA probes (both probes identical with probes from HER2 FISH pharmDx™ kit (K5331, Dako)); 15% N,N-dimethyl-acetamide (72336, Sigma-Aldrich); 20% dextran sulfate; 600 mM NaCl; 10 mM citrate buffer, pH 6.2

FISH Probe Composition II: 3.3 ng/µL HER2 TxRed labeled DNA probe (⅓ of standard concentration) (size 218 kb) and ½ of the standard concentration (300 nM) of CEN17 FITC labeled PNA probes (both probes identical with probes from HER2 FISH pharmDx™ kit (K5331, Dako)); 15% isobutyramide (144436, Sigma-Aldrich); 20% dextran sulfate; 600 mM NaCl; 10 mM citrate buffer, pH 6.2

| Composition | Background | Signal Intensity Tx Red FITC |
|---|---|---|
| I | +½ | 3 DNA 3 PNA |
| II | +½ | 3 DNA 3 PNA |

The scoring was performed on the mamma-carcinoma tissue of a multi-tissue section. Composition I and II were two phased at the used composition concentrations.

Example 4

This example compares the signal intensity and background from DNA probes and PNA probes on FFPE tissue sections using DMSO, at a denaturation temperature of 67° C. for 10 min and hybridization at 45° C. for 60 min.

FISH Probe Composition I: 3.3 ng/μL HER2 TxRed labeled DNA probe (⅓ of standard concentration) (size 218 kb) and ½ of the standard concentration (300 nM) of CEN17 FITC labeled PNA probes (both probes identical with probes from HER2 FISH pharmDx™ kit (K5331, Dako)); 15% ethylene carbonate (E2625-8, Sigma-Aldrich); 20% dextran sulfate; 600 mM NaCl; 10 mM citrate buffer, pH 6.2

FISH Probe Composition II: 3.3 ng/μL HER2 TxRed labeled DNA probe (⅓ of standard concentration) (size 218 kb) and ½ of the standard concentration (300 nM) of CEN17 FITC labeled PNA probes (both probes identical with probes from HER2 FISH pharmDx™ kit (K5331, Dako)); 15% DMSO (Sigma-Aldrich); 20% dextran sulfate; 600 mM NaCl; 10 mM citrate buffer, pH 6.2

| Composition | Background | Signal Intensity Tx Red FITC |
|---|---|---|
| I | +1½-2 | 3 DNA 2½ PNA |
| II | +2 | 1-2 DNA 2-2½ PNA |

The scoring was performed on the mamma-carcinoma tissue of a multi-tissue section. Composition II with DMSO was unclear in appearance (milky white) at the used composition concentrations.

The invention claimed is:

1. A hybridization composition comprising at least one nucleic acid sequence, at least one solvent in an amount effective to denature double-stranded nucleotide sequences, and a hybridization solution, wherein the solvent is chosen from tetrahydrothiophene 1-oxide, valerolactam, 1,3-dimethyl-3,4,5,6-tetrahydro-2(1H)-pyrimidinone, N,N-dimethyl-acetamide and isobutyramide.

2. The hybridization composition according to claim 1, wherein the solvent is a non-cyclic solvent.

3. The hybridization composition according to claim 1, wherein the solvent is chosen from N,N-dimethyl-acetamide, isobutyramide, and 1,3-dimethyl-3,4,5,6-tetrahydro-2(1H)-pyrimidinone.

4. The hybridization composition according to claim 1, wherein the concentration of solvent is about 1% to 95% (v/v).

5. The hybridization composition according to claim 1, wherein the concentration of solvent is 5% to 10% (v/v).

6. The hybridization composition according to claim 1, wherein the concentration of solvent is 10% to 20% (v/v).

7. The hybridization composition according to claim 1, wherein the concentration of solvent is 20% to 30% (v/v).

8. The hybridization composition according to claim 1, wherein the solvent is non-toxic.

9. The hybridization composition according to claim 8, wherein the composition contains less than 10% (v/v) formamide.

10. The hybridization composition according to claim 9, wherein the composition contains less than 2% (v/v) formamide.

11. The hybridization composition according to claim 10, wherein the composition contains less than 1% (v/v) formamide.

12. The hybridization composition according to claim 1, further comprising at least one additional component selected from the group consisting of: buffering agents, salts, accelerating agents, chelating agents, detergents, and blocking agents.

13. The hybridization composition according to claim 12, wherein the at least one additional component is an accelerating agent, a salt, and/or a buffering agent; and wherein the accelerating agent is dextran sulfate, the salt is NaCl, or the buffering agent is phosphate buffer.

14. The hybridization composition according to claim 13, wherein:
the NaCl is present at a concentration of up to 1200 mM, and/or
the phosphate buffer is present at a concentration of up to 50 mM.

15. The hybridization composition according to claim 14, wherein:
the NaCl is present at a concentration of 300 mM to 600 mM, and/or
the phosphate buffer is present at a concentration of 5 mM to 20 mM.

16. The hybridization composition according to claim 12, wherein the accelerating agent is selected from the group consisting of: formamide, glycerol, propylene glycol, 1,2-propanediol, diethylene glycol, ethylene glycol, glycol, and 1,3 propanediol, and the buffering agent is citric acid buffer.

17. The hybridization composition according to claim 16, wherein:
the formamide is present at a concentration of 0.1-5% (v/v),
the glycerol, propylene glycol, 1,2-propanediol, diethylene glycol, ethylene glycol, glycol, or 1,3 propanediol are present at a concentration of 0.1% to 10% (v/v), and
the citric acid buffer is present at a concentration of 1 mM to 50 mM.

18. The hybridization composition according to claim 1, comprising 40% (v/v) of the solvent, dextran sulfate, 300 mM NaCl, and 5 mM phosphate buffer.

19. The hybridization composition according to claim 1, comprising 15% (v/V) of the solvent, dextran sulfate, 600 mM NaCl, and 10 mM phosphate buffer.

20. The hybridization composition according to claim 1, comprising 15% (v/v) of the solvent, dextran sulfate, 600 mM NaCl, and 10 mM citric acid buffer pH 6.2.

* * * * *